United States Patent [19]

De Bruyn et al.

[11] Patent Number: 4,994,103
[45] Date of Patent: Feb. 19, 1991

[54] 1,5-SUBSTITUTED 1H-IMIDAZOLES

[75] Inventors: Marcel F. L. De Bruyn, Hoogstraten; Guy R. E. Van Lommen, Berlaar, both of Belgium; William R. Lutz, Riehen, Switzerland

[73] Assignees: Janssen Pharmaceutica N.V., Beerse, Belgium; Ciba-Geigy, Basel, Switzerland

[21] Appl. No.: 420,248

[22] Filed: Oct. 12, 1989

Related U.S. Application Data

[62] Division of Ser. No. 173,511, Mar. 25, 1988, Pat. No. 4,878,940.

[30] Foreign Application Priority Data

Apr. 2, 1987 [GB] United Kingdom ............... 87/07856
Dec. 22, 1987 [GB] United Kingdom ............... 87/29798

[51] Int. Cl.$^5$ .................. A01N 43/50; C07D 233/84; C07D 401/06; C07D 409/04
[52] U.S. Cl. ............................................ 71/92; 71/90; 546/256; 546/278; 548/336; 548/337; 548/341; 548/342; 548/343
[58] Field of Search ...................... 71/90, 92; 546/256, 546/278; 548/336, 342, 337, 341, 343

[56] References Cited

U.S. PATENT DOCUMENTS 3,485,917 12/1969 Godefroi et al. .................. 424/273
3,873,297  3/1975 Kupelian ............................. 71/78

FOREIGN PATENT DOCUMENTS 0216424  4/1987 European Pat. Off. .............. 233/64

Primary Examiner—John M. Ford
Attorney, Agent, or Firm—Charles J. Metz

[57] ABSTRACT

Novel herbicidal 1,5-substituted 1H-imidazole derivatives, compositions containing these compounds as active ingredients, and a method for controlling weeds, preferably selectively in crops of useful plants. Further the invention also relates to a process for making these novel compounds.

14 Claims, No Drawings

1,5-SUBSTITUTED 1H-IMIDAZOLES

This is a division of application Ser. No. 173,511, filed Mar. 25, 1988, now U.S. Pat. No. 4,878,940.

BACKGROUND OF THE INVENTION

A number of 1H-imidazole-5-carboxylic acid derivatives are known from U.S. Pat. No. 3,485,917 as antifungal agents. Further, some of these compounds are described as active agents in a method for inhibiting bud growth in U.S. Pat. No. 3,873,297. EP-A-216,424, published Apr. 1, 1987, discloses a group of imidazole-5-carbonyl or oxyiminoethyl derivatives having antifungal properties.

DESCRIPTION OF THE INVENTION

The present invention is concerned with 1H-imidazole derivatives having the formula

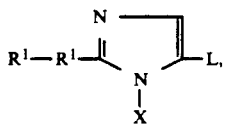

or a stereochemically isomeric form thereof, or a salt thereof,
wherein
$R^1$ is hydrogen or mercapto;
L is —C(=G)—R,

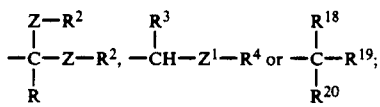

wherein
G is =N—$R^5$, oxygen or sulfur;
R is hydrogen, $C_1$-$C_7$alkyl, $C_3$-$C_7$cycloalkyl, fluoro$C_1$-$C_5$alkyl aryl$C_1$-$C_5$alkyl or aryl;
Z is oxygen or sulfur;
$Z^1$ is oxygen, sulfur or $NR^4$;
$R^2$ independently is $C_1$-$C_5$alkyl optionally substituted with phenyl, $C_5$-$C_7$cycloalkyl, $C_1$-$C_5$alkyloxy, $C_1$-$C_5$alkylthio or halo; or both $R^2$ radicals taken together may form a bivalent radical $CH_2$-$CH_2$ or $CH_2$-$CH_2$-$CH_2$ optionally substituted with $C_1$-$C_5$alkyl, hydroxy$C_1$-$C_5$alkyl, halo$C_1$-$C_5$alkyl or phenyl;
$R^3$ is hydrogen, $C_1$-$C_5$alkyl or fluoro$C_1$-$C_5$alkyl;
$R^4$ independently is hydrogen; aryl; $C_1$-$C_{12}$alkyl optionally substituted with aryl; $C_1$-$C_5$alkylcarbonyl; arylcarbonyl or $C_1$-$C_5$alkylaminocarbonyl;
$R^5$ is hydrogen, $C_1$-$C_5$alkyl or $OR^4$;
X is 1-indanyl, 1-tetrahydronaphthalenyl, 5-benzocycloheptanyl, 4-tetrahydrobenzothienyl, 4-tetrahydrobenzofuryl, 5-tetrahydroquinolyl, 5-tetrahydroisoquinolyl, 8-tetrahydroquinolyl, 8-tetrahydroisoquinolyl, 9,10-dihydro-9-antracenyl, 9H-fluoren-9-yl, 5-dibenzo[a,d]cycloheptenyl, 5-dibenzo[a,d]cycloheptanyl or 1-dihydronaphthalenyl each unsubstituted or substituted with one to six substituents selected from the group consisting of $C_1$-$C_5$alkyl, mono- and di(aryl) $C_1$-$C_5$alkyl, $C_1$-$C_5$alkyloxy, halo, $C_3$-$C_7$alkenyl, amino, nitro, $C_1$-$C_5$alkylcarbonylamino, trifluoromethyl and difluoromethoxy, wherein two geminal substituents together with the carbon atom to which they are attached may form a spirocyclic $C_3$-$C_7$cycloalkyl group, or two of said substituents taken together may form a $C_1$-$C_5$alkanediyl or $C_5$-$C_7$cycloalkanediyl group, said $C_1$-$C_5$alkanediyl or $C_5$-$C_7$cycloalkanediyl group being optionally substituted with one or two radicals independently selected from $C_1$-$C_5$alkyl, mono- and di-(aryl)$C_1$-$C_5$alkyl, $C_1$-$C_5$alkyloxy, halo, $C_3$-$C_7$alkenyl, trifluoromethyl, difluoromethoxy and aryl; or
X is a radical of formula

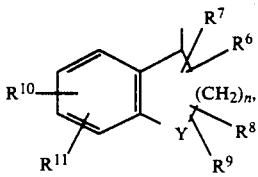

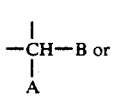

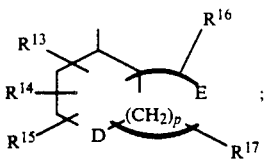

n is zero, one or two;
Y is a group —$CH_2$—O—, —$CH_2$—S(O)$_m$—, —$CH_2$—N—($R^{12}$)—, wherein the heteroatom is linked to the carbon atom of the benzene ring, and wherein m is zero, one or two;
$R^6$, $R^7$, $R^8$ and $R^9$ are each independently hydrogen, $C_1$-$C_5$alkyl, mono- and di(aryl)$C_1$-$C_5$alkyl, $C_1$-$C_5$alkyloxy, halo, $C_3$-$C_7$alkenyl, trifluoromethyl, difluoromethoxy or aryl; or
$R^6$ and $R^7$ together may form a fused benzene residue which optionally may be substituted with one or two substituents each independently selected from $C_1$-$C_5$alkyl, $C_1$-$C_5$alkyloxy, halo, $C_1$-$C_5$alkyl substituted with one to three halo atoms, $C_1$-$C_5$alkyloxy substituted with one to three halo atoms, nitro, amino and —NH—CO—M; or when $R^6$ and $R^7$ are geminally substituted, they may form, together with the carbon atom to which they are attached, a spirocyclic carbon ring with 3 to 7 carbon atoms; or $R^6$ and $R^7$ being substituted on different atoms, taken together may form a $C_1$-$C_5$alkanediyl or a $C_5$-$C_7$cycloalkanediyl group being optionally substituted with one or two radicals independently selected from $C_1$-$C_5$alkyl, mono- and di- aryl-$C_1$-$C_5$alkyl, $C_1$-$C_5$alkyloxy, halo, $C_3$-$C_7$alkenyl, trifluoromethyl, difluoromethoxy and aryl; and
$R^{10}$ and $R^{11}$ are each independently hydrogen, $C_1$-$C_5$alkyl, $C_1$-$C_5$alkyloxy, halo, trifluoromethyl, difluoromethoxy, cyano, nitro, amino, mono-and di-($C_1$-$C_5$alkyl)amino, or —NH—CO—M;
$R^{12}$ is hydrogen, $C_1$-$C_5$alkyl, $C_1$-$C_5$alkanoyl or 4-methylphenylsulfonyl;
A is $C_3$-$C_7$cycloalkyl optionally substituted with one or two $C_1$-$C_5$alkyl radicals; $C_1$-$C_7$alkyl optionally substituted with $C_1$-$C_7$alkyloxy or with an Ar radical; or $C_1$-$C_7$alkyl substituted with both a $C_1$-$C_7$alkyloxy and an Ar radical; or a radical selected from phenyl, pyridinyl, pyrimidinyl, naphthalenyl, furanyl and thienyl, each unsubstituted or substituted with one or two radicals, and in case A is phenyl also with three substituents independently selected from $C_1$-$C_5$alkyl, $C_1$-$C_5$alkyloxy, halo, nitro, amino, mono- and di-($C_1$-$C_5$alkyl)amino, —NH—CO—M, cyano, trifluoromethyl and difluoromethoxy;

said radical Ar being phenyl, pyridinyl, pyrimidinyl, naphthalenyl, furanyl or thienyl, each unsubstituted or substituted with one or two and in case Ar is phenyl also with three substituents independently selected from $C_1$-$C_5$alkyl, $C_1$-$C_5$alkyloxy, halo, nitro, amino, mono- and di-$C_1$-$C_5$alkylamino, —NH—CO—M, cyano, trifluoromethyl and difluoromethoxy;

B is naphthalenyl, thienyl, furanyl, pyrimidinyl, phenyl or pyridinyl, each unsubstituted or substituted with one or two substituents and in case B is phenyl also with three substituents independently selected from $C_1$-$C_5$alkyl, $C_1$-$C_5$alkyloxy, halo, cyano, nitro, amino, mono-and di-$C_1$-$C_5$alkylamino, —NH—CO—M, trifluoromethyl and difluoromethoxy; and M is $C_1$-$C_5$alkyl;

D is $CH_2$, O, $S(O)_m$ or $NR^{12}$;

p is 0, 1or 2;

E is a bivalent $C_1$-$C_5$alkanediyl or $C_3$-$C_5$alkenediyl radical;

$R^{13}$, $R^{14}$, $R^{15}$, $R^{16}$ or $R^{17}$ independently are hydrogen, $C_1$-$C_5$alkyl, mono- and di(aryl)$C_1$-$C_5$alkyl, hydroxyC$_1$-$C_5$alkyl, $C_1$-$C_5$alkyloxy$C_1$-$C_5$alkyl, $C_1$-$C_5$alkyloxy, $C_3$-$C_7$alkenyl, halo, trifluoromethyl, difluoromethoxy or aryl; or $R^{13}$ and $R^{14}$ being vicinally substituted may form an extra bond; or $R^{13}$ and $R^{14}$ taken together may form a $C_1$-$C_5$alkanediyl or $C_5$-$C_7$cycloalkanediyl radical, both being optionally substituted with $C_1$-$C_5$alkyl or $C_1$-$C_5$alkyloxy; and each aryl independently is phenyl optionally substituted with one to three substituents each independently selected from $C_1$-$C_5$alkyl, $C_1$-$C_5$alkyloxy and halo;

$R^{18}$ is hydrogen, $C_1$-$C_5$alkyl or halo;

$R^{19}$ is hydrogen or halo; and $R^{20}$ is halo.

In the foregoing definitions, $R^{13}$, $R^{14}$ and $R^{15}$ may be substituted on any carbon atom making up the ring containing D, including the group D being $CH_2$, and the carbon atoms connected to the radical E.

Surprisingly, the compounds of formula (I) exhibit strong herbicidal properties, and are therefore useful to control weeds. This property gains importance by the fact, that some crops of useful plants are not damaged, or are only slightly harmed when treated with compounds of formula (I) at high dosages. Consequently, the compounds of formula (I) are valuable selective herbicides in crops of useful plants, such as sugar-beet, rape, soybeans, cotton, sunflower, cereals, especially wheat, barley, rye and oats, rice, both upland rice and paddy rice, and maize. Especially in rice crops a broad range of application rates can be employed, preferably if the rice crops are transplanted rice crops, and if the compounds of formula (I) are applied after transplantation. In maize crops selective herbicidal action is observed both at preemergence and at postemergence treatment.

The active ingredients (a.i.) of formula (I) are usually applied at application rates of 0.01 to 5.0 kg of active ingredient per hectare in order to achieve satisfying results. Sometimes, depending on the environmental conditions, the application rates may exceed the above designated limitations. However, the preferred application rates are between 0.05 kg and 1.0 kg a.i. per hectare.

As used in the foregoing definitions $C_1$-$C_5$alkyl denotes straight or branch chained saturated hydrocarbon radicals having from 1 to 5 carbon atoms, e.g. methyl, ethyl, propyl, 1-methylethyl, the four butyl isomers and the pentyl isomers; $C_1$-$C_7$ and $C_1$-$C_{12}$alkyl include $C_1$-$C_5$alkyl radicals and the higher homologs thereof having respectively up to 7 to 12 carbon atoms; halo is fluoro, chloro, bromo or iodo, with fluoro and chloro being preferred; $C_3$-$C_7$alkenyl defines straight and branch chained hydrocarbon radicals containing one double bond and having from 3to 7 carbon atoms such as, for example, 2-propenyl, 3-butenyl, 2-butenyl, 2-pentenyl, 3-pentenyl, 2-methyl-2-propenyl, or 3-methyl-2-butenyl, with 2-propenyl and 2-methyl-2-propenyl being preferred; $C_3$-$C_7$cycloalkyl is generic to cyclopropyl, cyclobutyl, cyclopentyl, cyclohexyl and cycloheptyl, with cyclopentyl and cyclohexyl being preferred; $C_5$-$C_7$cycloalkyl is generic to cyclopentyl and and cyclohexyl; $C_1$-$C_5$alkyloxy denotes, for example, methoxy, ethoxy, propyloxy, 1-methylethyloxy, the four butyloxy isomers or the pentyloxy isomers; $C_1$-$C_5$alkylthio denotes, for example, methylthio, ethylthio, 1-propylthio, 1-methylethylthio, the four butylthio-isomers or the pentylthio-isomers; $C_1$-$C_5$alkanoyl denotes formyl, acetyl, propionyl, butyryl, isobutyryl, valeryl, isovaleryl or pivaloyl; fluoro$C_1$-$C_5$alkyl denotes mono- or polyfluoro substituted saturated hydrocarbon radicals, i.e. $C_1$-$C_5$alkyl radicals wherein from one up to all hydrogen atoms are replaced by fluor atoms such as, for example, fluoromethyl, difluoromethyl, trifluoromethyl, fluoroethyl, trifluoroethyl, pentafluoroethyl, trifluoropropyl, heptafluoropropyl; halo$C_1$-$C_5$alkyl defines $C_1$-$C_5$alkyl radicals being substituted with up to three halo atoms such as, for example, fluoromethyl, difluoromethyl, trifluoromethyl, chloromethyl, trichloromethyl, 1,1,1-trifluoroethyl and the like.

As typical examples of mono-and di-(aryl)$C_1$-$C_5$alkyl there may be mentioned phenylmethyl, phenylethyl, 4-chlorophenylmethyl, 4-chlorophenylethyl, 4-methoxyphenylmethyl, 3-methoxyphenylmethyl or diphenylmethyl with phenylmethyl being preferred. $C_1$-$C_4$alkanediyl denotes straight or branch chained bivalent saturated hydrocarbon radicals having from 1 to 4 carbon atoms; $C_1$-$C_5$alkanediyl includes $C_1$-$C_4$alkanediyl radicals and the higher homologs thereof having 5 carbon atoms. $C_3$-$C_5$alkenediyl d enotes straight or branched chained bivalent hydrocarbon radicals containing a double bond and having from 3 to 5 carbon atoms. $C_5$-$C_7$cycloalkanediyl defines bivalent cyclic hydrocarbon radicals having from 5 to 7 carbon atoms, i.e. cyclopentanediyl, cyclohexanediyl or cycloheptanediyl.

The condensed cyclic ring systems being defined under symbol X and being attached to the 1-position of the imidazole ring encompass the following principle structures, which may be unsubstituted or substituted with the substituents as defined:

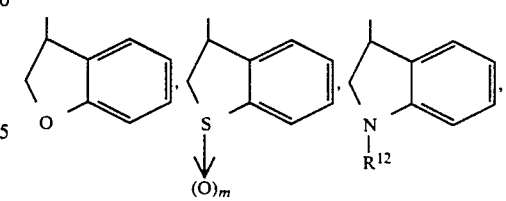

-continued

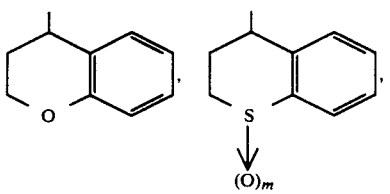

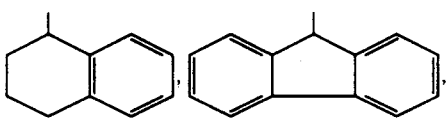

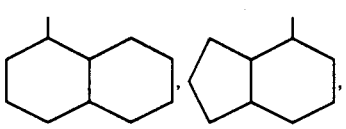

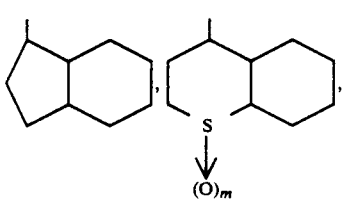

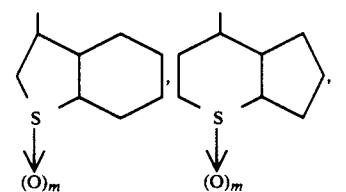

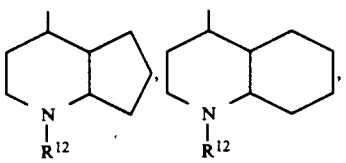

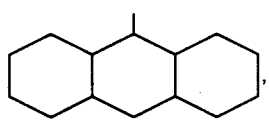

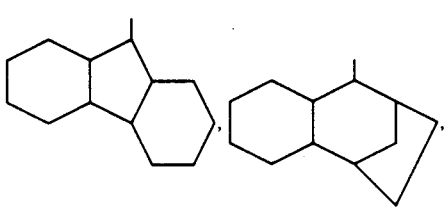

-continued

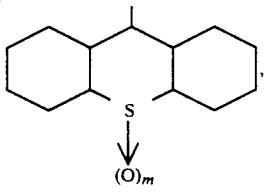

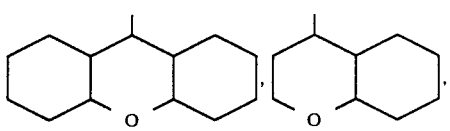

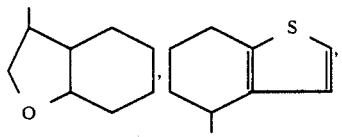

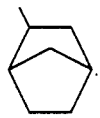

As defined hereinabove, when $R^6$ and $R^7$ are attached to adjacent carbon atoms, they may form an optionally substituted benzene ring with said adjacent carbon atoms. As a result, the Y-containing heterocycle is fused with two benzene rings.

As further defined hereinabove, when $R^6$ and $R^7$ are attached to the same carbon atom, they may form a spirocyclic ring together with said carbon atom. Typical embodiments of such spirocyclic rings are cyclopropane, cyclobutane, cyclopentane, cyclohexane and cycloheptane.

Depending on the nature of the moiety X linked to the imidazole in position 1 and/or the group L, the compounds of formula (I) may contain asymmetrical carbon atoms. Unless otherwise mentioned or indicated, the chemical designation of compounds denotes the mixtures of all stereochemically isomeric forms. These mixtures contain all diastereomers and enantiomers of the basic molecular structure. The absolute configuration of each chiral center may be indicated by the stereochemical descriptors R and S and the relative configuration of vicinal substituents on a double bond may be indicated by the stereochemical descriptors E and Z, this R and S and E and Z notation corresponding to the rules described in Pure Appl. Chem. 1976, 45, 11-30. The relative configuration of the asymmetric centers in the compounds of formula (I) is denoted by cis and trans and where appropriate by the terms α and β, these sterochemical descriptors being used according to the rules described in Chemical Abstracts 1977 Index Guide, Appendix IV, §203.

Pure isomeric forms of these compounds can be separated from the mixtures by conventional separation methods. Preferably, if a specific stereochemical form is desired, said compound will be synthesized by stereoselective methods of preparation. These methods will advantageously employ pure forms of optically active starting materials.

The invention also comprises the salts which the compounds of formula (I) are able to form with organic or inorganic acids, such as mineral acids, sulfonic acids, carboxylic acids or phosphorus containing acids.

Examples of salt-forming mineral acids are hydrofluoric acid, hydrochloric acid, hydrobromic acid, hydroiodic acid, sulfuric acid, nitric acid, chloric acid, perchloric acid or phosphoric acid. Preferred salt-forming sulfonic acids are 4-methylbenzenesulfonic acid, benzenesulfonic acid, methanesulfonic acid or trifluoromethanesulfonic acid. Preferred salt-forming carboxylic acids are acetic acid, trifluoroacetic acid, benzoic acid, chloroacetic acid, phthalic acid, maleic acid, malonic acid and citric acid. Phosphorus containing acids are the various phosphonous acids, phosphonic acids and phosphinic acids.

A particular subgroup of compounds of formula (I) comprises those compounds of formula (I) wherein L is other than a radical —$CR^{18}R^{19}R^{20}$ Among the latter compounds, a further particular subgroup comprises those compounds wherein X is other than a radical of formula (c).

Preferred compounds within the scope of formula (I) are those compounds of formula (I), or those compounds of formula (I) pertaining to either one of the above defined particular subgroups wherein (a) X is 1-indanyl, 1-tetrahydronaphthalenyl, 5-tetrahydrobenzothienyl, 4-tetrahydrobenzofuryl, each substituted or unsubstituted with up to six substituents and in particular up to 4 substituents independently selected from $C_1$-$C_5$alkyl, $C_1$-$C_5$alkyloxy, halo, $C_3$-$C_7$alkenyl, amino, nitro, trifluoromethyl or difluoromethoxy wherein two geminal substituents together with the carbon to which they are attached may form a spirocyclic $C_3$-$C_7$cycloalkyl group; or two of said substituents taken together may form a $C_1$-$C_5$alkanediyl group being optionally substituted with one or two radicals independently selected from $C_1$-$C_5$alkyl, $C_1$-$C_5$alkyloxy, halo, trifluoromethyl or difluoromethoxy; or X is a radical of formula (a) wherein Y is a group —$CH_2O$— or —$CH_2S(O)_m$—; $R^6$, $R^7$, $R^8$ and $R^9$ are each independently hydrogen, $C_1$-$C_5$alkyl, $C_1$-$C_5$alkyloxy, halo, $C_3$-$C_7$alkenyl, trifluoromethyl or difluoromethoxy;

X is a radical of formula (b) wherein A is $C_3$-$C_7$cycloalkyl optionally substituted with one or two $C_1$-$C_5$alkyl radicals; $C_1$-$C_7$alkyl optionally substituted with $C_1$-$C_7$alkyloxy or Ar; or A is phenyl, pyridinyl, pyrimidinyl, naphthalenyl or thienyl, each unsubstituted or substituted with one or two radicals or in case A is phenyl with 3 substituents independently selected from $C_1$-$C_5$alkyl, $C_1$-$C_5$alkyloxy, halo, nitro, amino, cyano, trifluoromethyl or difluoromethoxy; or X is a radical (c) wherein D is $CH_2$, O, $S(O)_m$; and/or (b) L is —C(=G)—R, wherein G is O, S or $NR^5$, wherein $R^5$ is hydrogen, $C_1$-$C_5$alkyl, $C_1$-$C_6$alkyloxy or hydroxy; R is hydrogen, $C_1$-$C_7$alkyl, $C_3$-$C_7$cycloalkyl or fluoro$C_1$-$C_5$alkyl; or L is —CR—$(ZR^2)_2$ wherein R is hydrogen, $C_1$-$C_7$alkyl, $C_3$-$C_7$cycloalkyl or fluoro$C_1$-$C_5$alkyl; $R^2$ independently is $C_1$-$C_5$alkyl or both $R^2$ radicals taken together may form a bivalent $CH_2$—$CH_2$ or $CH_2$—$CH_2$—$CH_2$ radical optionally substituted with $C_1$-$C_5$alkyl; or L is

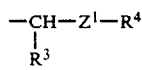

wherein $R^4$ is hydrogen, $C_1$-$C_6$alkyl, $C_1$-$C_5$alkylcarbonyl or $C_1$-$C_5$alkylaminocarbonyl; $Z^1$ is O, S or $NR^4$ wherein $R^4$ is hydrogen, $C_1$-$C_6$alkyl, $C_1$-$C_5$alkylcarbonyl or $C_1$-$C_5$alkylaminocarbonyl; or L is

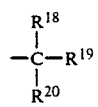

wherein $R^{18}$ is hydrogen, $C_1$-$C_5$alkyl, fluoro or chloro; $R^{19}$ is hydrogen, fluoro or chloro; $R^{20}$ is fluoro or chloro.

Particularly preferred compounds of formula (I) are those preferred compounds wherein (a) X is 1-indanyl, 1-tetrahydronaphthalenyl, 5-tetrahydrobenzothienyl, 4-tetrahydrobenzofuryl, each unsubstituted or substituted in their benzene part with up to three, and in particular up to two substituents, independently selected from $C_1$-$C_5$alkyl, $C_1$-$C_5$alkyloxy, halo, amino, nitro, trifluoromethyl or difluoromethoxy; and/or in their non-benzenic part with up to three, and in particular up to two, substituents independently selected from $C_1$-$C_5$alkyl, $C_1$-$C_5$alkyloxy, halo, trifluoromethyl and difluoromethoxy; or two geminal substituents together with the carbon atom to which they are attached may form a spirocyclic $C_3$-$C_7$alkyl ring; or two of non-benzenic substituents taken together may form a $C_1$-$C_5$alkanediyl group optionally substituted with $C_1$-$C_5$alkyl; or X is a radical of formula (a) wherein $R^6$ and $R^7$ independently are hydrogen, $C_1$-$C_5$alkyl, $C_1$-$C_5$alkyloxy or halo; or $R^6$ and $R^7$ taken together with the carbon atom to which they are attached may form a spirocyclic $C_3$-$C_7$cycloalkyl ring; or $R^6$ and $R^7$ taken together may form a $C_1$-$C_5$alkanediyl radical; and $R^8$ and $R^9$ independently are hydrogen or $C_1$-$C_5$alkyl; $R^{10}$ and $R^{11}$ independently are hydrogen, $C_1$-$C_5$alkyl, $C_1$-$C_5$alkyloxy, halo, trifluoromethyl, difluoromethoxy, cyano, nitro or amino; or X is a radical of formula (b) wherein A is $C_1$-$C_7$alkyl optionally substituted with Ar, wherein Ar is phenyl, pyridinyl, pyrimidinyl, naphthalenyl, furanyl or thienyl each unsubstituted or substituted with one or two, or in case Ar is phenyl with up to 3 substituents independently selected from $C_1$-$C_5$alkyl, $C_1$-$C_5$alkyloxy, halo, cyano, trifluoromethyl and difluoromethoxy; or A is phenyl, pyridinyl, pyrimidinyl, naphthalenyl, furanyl or thienyl each unsubstituted or substituted with one or two, or in case A is phenyl with 3 substituents independently selected from $C_1$-$C_5$alkyl, $C_1$-$C_5$alkyloxy, halo, trifluoromethyl and difluoromethoxy; wherein B is naphthalenyl, thienyl, furanyl, pyrimidinyl, phenyl or pyridinyl, each unsubstituted or substituted with one or two and in case B is phenyl also with 3 substituents independently selected from $C_1$-$C_5$alkyl, $C_1$-$C_5$alkyloxy, halo, cyano, trifluoromethyl or difluoromethoxy; or X is a radical (c) wherein p is 0 or 1, $R^{13}$ and $R^{14}$ independently are hydrogen, $C_1$-$C_5$alkyl, hydroxy$C_1$-$C_5$alkyloxy$C_1$-$C_5$alkyl or trifluoromethyl; or $R^{13}$ and $R^{14}$ being vicinally substituted may form an extra bond; or $R^{13}$ and $R^{14}$ taken together may form a $C_1$-$C_5$alkanediyl radical optionally substituted with $C_1$-$C_5$alkyl; $R^{15}$ is hydrogen or $C_1$-$C_5$alkyl; $R^{16}$ and $R^{17}$ independently are hydrogen, $C_1$-$C_5$alkyl, hydroxy$C_1$-$C_5$alkyl, $C_1$-$C_5$alkyloxy$C_1$-$C_5$alkyl or trifluoromethyl; and/or (b) L is —C(=G)—R wherein G is O or $NR^5$, wherein $R^5$ is hydrogen, $C_1$-$C_5$alkyl or hydroxy; R is hydrogen, $C_1$-$C_7$alkyl or fluoro$C_1$-$C_5$alkyl; or L is —CR(ZR$^2$)$_2$ wherein R is hydrogen, C$_1$-C$_7$alkyl or fluoroC$_1$-C$_5$alkyl;

R$^2$ independently is C$_1$-C$_5$alkyl, or both R$^2$ radicals taken together may form a bivalent radical CH$_2$—CH$_2$ or CH$_2$—CH$_2$—CH$_2$; or L is

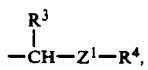

wherein R$^4$ is hydrogen, C$_1$-C$_5$alkyl; Z$^1$ is O, S or NR$^4$ wherein R$^4$ is hydrogen, C$_1$-C$_5$alkyl.

More particularly preferred compounds are those particularly preferred compounds wherein (a) X is 1-indanyl or 1-tetrahydronaphthlenyl each unsubstituted or substituted in their benzene part with up to two substituents each independently selected from C$_1$-C$_5$alkyl, C$_1$-C$_5$alkyloxy or halo; and in their non-benzenic part with up to two C$_1$-C$_5$alkyl substituents or two substituents in the non-benzenic part together with the carbon atom to which they are attached may form a spiroC$_3$-C$_7$alkyl ring; or X is a radical of formula (a) wherein R$^6$ and R$^7$ independently are hydrogen or C$_1$-C$_5$alkyl; R$^8$ and R$^9$ are hydrogen; R$^{10}$ and R$^{11}$ independently are hydrogen, C$_1$-C$_5$alkyl, C$_1$-C$_5$alkyloxy or halo; Y is —CH$_2$—O— or —CH$_2$—S—; or X is a radical of formula (b) wherein A is C$_1$-C$_7$alkyl, phenyl or pyridinyl, the latter two being optionally substituted with up to two radicals independently selected from C$_1$-C$_5$alkyl, halo and C$_1$-C$_5$alkyloxy; B is phenyl or pyridinyl, optionally substituted with up to two radicals independently selected form C$_1$-C$_5$alkyl, halo and C$_1$-C$_5$alkyloxy; or X is a radical of formula (c) wherein D is CH$_2$, O or S and R$^{13}$ and R$^{14}$ independently are hydrogen or C$_1$-C$_5$alkyl; or R$^{13}$ and R$^{14}$ taken together form a C$_1$-C$_5$alkanediyl radical; R$^{15}$ is hydrogen; E is a bivalent C$_1$-C$_5$alkanediyl radical; R$^{16}$ and R$^{17}$ independently are hydrogen or C$_1$-C$_5$alkyl; and/or (b) L is —C(=O)—R wherein R is hydrogen, C$_1$-C$_7$alkyl or fluoroC$_1$-C$_5$alkyl;

L is —CR(OR$^2$)$_2$ wherein R is hydrogen, C$_1$-C$_7$alkyl or fluoroC$_1$-C$_5$alkyl;

L is —CH—O—R$^4$, wherein R$^4$ is hydrogen or C$_1$-C$_6$alkyl; R$^3$

L is difluoromethyl, fluoromethyl, chloromethyl, trifluoromethyl or trichloromethyl.

Still more particularly preferred compounds are those more particularly preferred compounds wherein X is 1-indanyl or 1-tetrahydronaphthalenyl being optionally substituted in the benzene part with up to two halo's, and in particular with up to two fluoro or chloro atoms; and being optionally substituted in the non-benzenic part with C$_1$-C$_5$alkyl, in particular with C$_1$-C$_2$alkyl;

X is a radical of formula (a) wherein Y is —CH$_2$—O— or —CH$_2$—S—, n is zero or one; R$^6$ and R$^7$ are hydrogen or C$_1$-C$_5$alkyl or in particular hydrogen or C$_1$-C$_2$alkyl; R$^{10}$ and R$^{11}$ are hydrogen or halo, in particular chloro or fluoro;

X is a radical of formula (b) wherein A is C$_1$-C$_7$alkyl, in particular C$_3$-C$_7$alkyl, or A is phenyl or pyridinyl, both being optionally substituted with C$_1$-C$_5$alkyl, methoxy or halo, or in particular with C$_1$-C$_2$alkyl, methoxy, chloro or fluoro; B is pyridinyl or phenyl optionally substituted with C$_1$-C$_5$alkyl, methoxy or halo, or in particular with C$_1$-C$_2$alkyl, methoxy, chloro or fluoro;

X is a radical of formula (c) wherein D is CH$_2$, O or S; p is 0 or 1; R$^{13}$ and R$^{14}$ are hydrogen or C$_1$-C$_5$alkyl, and in particular hydrogen or C$_1$-C$_2$alkyl; E is C$_3$-C$_4$alkanediyl; R$^{16}$ and R$^{17}$ are hydrogen or C$_1$-C$_5$alkyl and in particular hydrogen or C$_1$-C$_2$alkyl.

Among the compounds of formula (I), the particular groups of compounds of formula (I), the preferred, particular preferred and more particular preferred groups of compounds of formula (I), special preference is given to those compounds within said groups wherein R$^1$ is hydrogen.

Most preferred compounds are 1-[1-(2,3-dihydro-2,2-dimethyl-1H-inden-1-yl)-1H-imidazol-5-yl]ethanone, 1-[1-(1,2,3,4-tetrahydro-1-naphthalenyl)-1H-imidazol-5-yl]ethanone and 1-(diphenylmethyl)-α-methyl-1H-imidazol-5-methanol.

The preparation of the compounds of formula (I) is generally carried out by the following methods.

The compounds of formula (I) wherein L is —C(=O)—R can be obtained by condensing a compound of formula

wherein X and R are as defined hereinabove, with a C$_1$-C$_4$alkyl ester of formic acid in the presence of a suitable base such as, for example, an alkali metal alkoxide or hydride, e.g. sodium methoxide, potassium ethoxide, sodium hydride, lithium hydride, and the like, in a reaction-inert solvent; and treating the resultant intermediate of formula

wherein X and R are as defined hereinabove and Q is an alkali metal atom, either (a) with an alkali metal isothiocyanate in the presence of an acid, thus obtaining a 2-mercaptoimidazole of formula

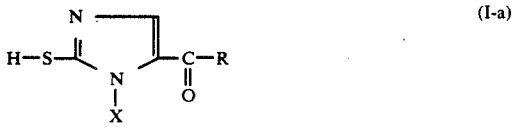

wherein X and R are as defined hereinabove, which optionally is converted into a compound of the formula

wherein X and R are as defined hereinabove, by reacting the starting compound with nitric acid optionally in the presence of an alkali metal nitrite, e.g. sodium nitrite; or with Raney-nickel in the presence of a $C_1$-$C_6$alkanol, preferably ethanol, at a temperature between 40° C. and 80° C.; or also by treating the starting compounds with an aqueous hydrogen peroxide solution preferably in the presence of a carboxylic acid, in particular a $C_1$-$C_6$alkanoic acid, e.g. acetic acid; or (b) with a carboxylic acid amide of 1 to 3 carbon atoms, preferably formamide, in the presence of an acid at a temperature between 50° C. and 250° C., preferably between 120° C. and 170° C.; or (c) with an excess of ammonium carbonate or hydrogen carbonate in a suitable solvent, which may be a reaction-inert solvent and/or an acid, at a temperature between 20° C. and 200° C., preferably between 25° C. and the reflux temperature of the reaction mixture.

In the afore-mentioned processes reaction-inert solvents are, for example, aromatic hydrocarbons such as benzene, methylbenzene or dimethylbenzene; ethers such as, for example, 1,1'-oxybisethane, tetrahydrofuran or 1,4-dioxane; or other aprotic organic solvents. For the cyclization-reaction of the imidazole ring structure, strong mineral acids such as hydrohalic acids, e.g. hydrochloric acid, are most conveniently employed. In the ring-forming variant (c) also other acids, e.g. acetic acid, can be used. In this reaction an excess of acid of 5 to 50, preferably of 15 to 40 times the required molar amount is most preferably used. The excess of ammonium salt in this process is 2 to 50, preferably 10 to 30 times the required molar amount.

The compounds of formula (I-b) can also be prepared by the deamination reaction of a 4-amino-1H-imidazole derivative of formula (IV), wherein R and X are as defined under formula (I). Said deamination reaction involves a diazotation and a reductive dediazotation step which may be conducted sequentially, i.e. with isolation of the intermediate diazonium salt (IV-a) or in a one-pot fashion wherein said diazonium salt is reduced in situ.

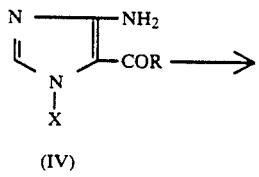

(IV)

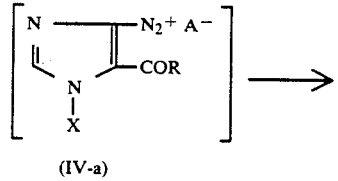

(IV-a)

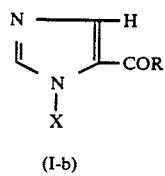

(I-b)

Treatment of the 4-amino-1H-imidazole derivative of formula (IV) in aqueous medium with an alkali metal nitrite, e.g. sodium or potassium nitrite, in the presence of an acid such as hydrochloric acid, sulfuric acid or nitric acid, or with nitronium tetrafluoroborate ($NO^+BF_4^-$) yields the diazonium salt (IV-a). In the latter, R and X are as defined under formula (I) and $A^-$ represents an anion corresponding to the conjugated base of the acid employed in the diazotation reaction or the tetrafluoroborate anion. The intermediate diazonium salts (IV-a) are reduced to the compounds of formula (I-b) by treatment with an appropriate reductant such as hypophosphoric acid at an elevated temperature, preferably at the boiling temperature of the reaction mixture.

Alternatively, treatment of the 4-amino-1H-imidazole derivatives of formula (IV) with a $C_1$-$C_5$alkyl nitrite such as, 1,1-dimethylethyl nitrite or 1,2-dimethylpropyl nitrite in suitable aprotic solvent such as tetrahydrofuran, 1,4-dioxane, trichloromethane or N,N-dimethylformamide yields a compound of formula (I-b) directly. The latter deamination reaction may conveniently be conducted at an elevated temperature, generally at the boiling point of the reaction mixture.

The compounds of formula (I) wherein $R^1$ is hydrogen and L is $-C(=NH)-R$, wherein the radical R is not hydrogen, said radical being represented by $R^a$ and said compounds by (I-c) can be prepared by reacting a cyanide of formula

(V)

wherein X is as defined hereinabove, with a Grignard reagent of formula

$R^a-Mg-Y$ (VI)

wherein Y is halo, in a suitable solvent such as an ether, e.g. tetrahydrofuran, 1,1'-oxybisethane and the like, thus obtaining an imine of formula

(I-c)

The latter compound of formula (I-c) can be hydrolysed to obtain the corresponding keto-compound of formula (I-b) wherein R is $R^a$.

The compounds of formula (I) wherein $R^1$ preferably is hydrogen and L is $-CH_2-NH_2$ can be obtained by reducing a cyanide of formula (V), e.g. by reacting the cyanide (V) with a suitable reducing agent such as, for example, a complex metal hydride, e.g. lithium tetrahydroaluminate; hydrogen in the presence of a noble metal catalyst; or Raney nickel in a suitable reaction-inert solvent, for example an alkanol, e.g. methanol, ethanol and the like. Similarly, the imines of formula (I-c) can be reduced to compounds of formula (I) wherein L is $-CHR^a-NH_2$.

In a number of the following preparations it is expedient that the mercapto group ($R^1$ is mercapto) is protected, prior to further conversion. Suitable protective groups are, for instance, triphenylmethyl, acetamidomethyl, ethylcarbamoyl and the like groups.

The compounds of formula (I) wherein L is $-CH_2-N(R^{21})_2$ and each $R^{21}$ independently is hydrogen or $C_1$-$C_{12}$alkyl optionally substituted with aryl, may be obtained by reducing an imidazole carboxylic amide of formula

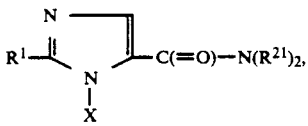

(VII)

wherein X and R²¹ are as defined hereinabove. Said reduction can conveniently be conducted by treating the amide (VII) with an appropriate reducing agent such as, for example, lithium tetrahydroaluminate; sodium borohydride in the presence of a cobalt (II) salt, e.g. cobalt chloride or of a carboxylic acid, e.g. acetic acid or trifluoroacetic acid; borane; or trichlorosilane in a suitable reaction-inert solvent such as, for example, an ether, e.g. 1,1'-oxybisethane, tetrahydrofuran, 1,4-dioxane, 1,1'-oxybis(2-methoxyethane) and the like; an aromatic hydrocarbon, e.g. benzene, methylbenzene, dimethylbenzene and the like; or a mixture of such solvents. Said reduction may be conducted at temperatures ranging from room temperature to the boiling point of the reaction mixture, preferably at the boiling point of the reaction mixture.

The compounds of formula (I) wherein L is —CH₂OH can be obtained by reducing an imidazole carboxylic acid or ester of formula

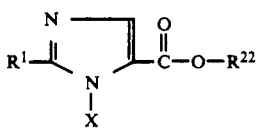

(VIII)

wherein R¹ and X are as defined hereinabove and R²² is hydrogen or C₁₋₅alkyl optionally substituted with aryl. Said reduction reaction can conveniently be performed by reacting (VIII) with a complex metal hydride such as lithium tetrahydroaluminate or sodium dihydrobis(2-methoxyethoxy) aluminate in a suitable solvent such as an ether, e.g., tetrahydrofuran, 1,1'-oxybisethane, a hydrocarbon e.g. benzene, methylbenzene or mixtures of such solvents.

The carboxylic acid esters of formula (VIII) may be converted into corresponding compounds of formula (I) wherein L is —C(=O)—Rᵃ upon treatment with a Grignard reagent of formula Rᵃ-Mg-Y (VI) or an organolithium reagent Rᵃ-Li, in an appropriate reaction-inert solvent, such as an ether, e.g. tetrahydrofuran, 1,1'-oxybisethane and the like. In order to suppress the formation of tertiary alcohols, it may be appropriate to conduct the reaction at low temperature optionally in the presence of a metallic halide catalyst, notably ferric or cuprous halide, or in the presence of a trialkylamine, e.g. N,N-diethylethanamine and the like.

The compounds of formula (I) wherein L is CHO may be obtained from (VII) or (VIII) following art-known reduction procedures. Suitable reagents for said reduction are, for example, lithium tri-t-butoxyaluminum hydride, diisobutylaluminum hydride, dialkylaminoaluminum hydrides, sodium aluminum hydride and the like. It may be appropriate to conduct the reaction at low temperatures, generally at temperatures in the range of −78° C. to 0° C., in particular between −78° C. and −60° C.

The compounds of formula (I) can also be converted into each other following art-known functional group transformation reactions.

The substituent L may be transformed to other substituents encompassed by the definition of L by suitable reactions known in the art for the modification of ketones, aldehydes, alcohols, amines and imines.

The compounds of formula (I) wherein L is —C(=O)—R³ can be obtained by oxidizing the corresponding alcohols of formula (I) (L is —CH(R³)—OH), e.g. by reacting the alcohols with a suitable oxidant such as, for example, manganese(IV) oxide in an inert solvent, e.g. 1,4-dioxane, tetrahydrofuran, 1,1'-oxybisethane, 2-propanone, 4-methyl-2-pentanone and the like; an earth alkaline metal manganate, such as, for example barium manganate in an inert solvent such as, for example, a halogenated hydrocarbon e.g. dichloromethane; chromium (VI) oxide and derived reagents in an inert solvent; or by electrochemical oxidation of said alcohols.

The compounds of formula (I) wherein L is —CH(C₁-C₅alkyl)—OH can be obtained by reacting a compound of formula (I) wherein L is —CH=O with a Grignard reagent of formula (C₁-C₅alkyl)MgY wherein Y is halo, in a suitable solvent such as an ether, e.g. 1,1'-oxybisethane, tetrahydrofuran and the like.

The compounds of formula (I) wherein L is —CH(R³)—Z¹—H can be acylated with an appropriate reagent according to art-known acylation procedures, e.g. by reacting the alcohol, amine, or mercaptan with a carboxylic acid halide or anhydride or with a C₁-C₅alkylisocyanate.

The compounds of formula (I) wherein L is a radical of formula —C(=G¹)—R and G¹ is oxygen or sulfur, may be acetalized or thioacetalized to yield the acetal or thioacetal compounds wherein L is —C(R)(Z—R²)—Z—R². Said acetalization reaction may conveniently be conducted following art-known procedures such as, for example, by reacting the starting material with an alcohol, diol, thiol or dithiol in the presence of an appropriate acid, preferably with removal of the reaction products which are formed during the course of the reaction. Conversely, the latter compounds may be hydrolyzed to yield the corresponding oxo or thio compounds, e.g. by treating the starting acetals or thioacetals with an aqueous acidic medium.

The compounds of formula (I) wherein L is —C(=O)—R can be converted to the corresponding thiones wherein L is —C(=S)—R by treatment with diphosphorus pentasulfide or with 2,4-bis(4-methoxyphenyl)-2,4-disulfide-1,3,2,4-dithiadiphosphetane (Lawesson's reagent). The former compounds can also be converted into the corresponding compounds wherein L is —C(=NR⁵)—R by treatment with a reagent of formula H₂N—R⁵.

Y or D being —CH₂—S— or respectively —S— may be converted to the corresponding sulfoxide or sulfone by an appropriate oxidation procedure, e.g. by treatment with a peroxide or a periodate.

The compounds of formula (I) wherein L is a halogenated C₁-C₆alkyl radical (L is CR¹⁸R¹⁹R²⁰), can be obtained following art-known halogenation procedures. For instance, the compounds wherein L is a monohaloC₁-C₆alkyl group, can be derived from analogous monohydroxyC₁-C₆alkyl derivatives wherein L is —CHOH—R³, by treatment with a halogenating reagent such as, for example, thionyl chloride, thionyl bromide, oxalyl chloride, phosphorus trichloride, phosphorus tribromide, phosphoryl chloride, phosphoryl bromide, phosphorus and iodine, diethylaminosulfur trifluoride and the like reagents. The compounds wherein L is a geminally substituted dihaloC$_1$-C$_6$alkyl group, can be obtained from the corresponding carbonyl derivatives wherein L is —C(=O)R upon treatment with a suitable halogenating reagent such as, for example, pentachlorophosphorane, phosphorus trichloride, phosphorus tribromide, phosphoryl chloride, phosphoryl bromide, oxalyl chloride, diethylaminosulfur trifluoride, 1,2-phenyldioxytrichlorophosphorane, 1,1-diclorooxybismethane and the like reagents. The compounds wherein L is a trihalomethyl group may be derived from intermediates wherein L is mono- or dihalomethyl by photochemical halogenation. Said halogenation reactions can conveniently be conducted in the presence of a suitable reaction-inert solvent. Most of the above-mentioned procedures are in general terms disclosed in basic text books of organic chemistry. A number of special methods are reported in for example, J. Org. Chem., 1975, 40, 574, Houben-Weyl, Methoden den Organischen Chemie, Vol 5(3), 1962, pp. 84-93, 899, 905-912, 955, Ber. Dtsch. Chem. Ges. 1959, 92, 83 and Ber. Dtsch. Chem. Ges. 1963, 96, 1387.

The compounds of formula (I) wherein L is monohaloC$_1$-C$_6$alkyl group, halo preferably being chloro or bromo, can be converted into compounds wherein L is —CH(R$^3$)—Z$^1$—C$_1$-C$_6$alkyl by reaction with a reagent H—Z$^1$—C$_1$-C$_6$alkyl. In some instances it may be advantageous to convert said reagent first into a metal salt thereof, preferably the sodium salt, e.g. by treatment with a metal base such as sodium hydride, sodium hydroxide; an alkali metal, e.g. sodium and the like; and to use said metal salt subsequently in the reaction with said monohaloC$_1$-C$_6$alkyl derivative.

In a similar manner, the compounds of formula (I) wherein L is a geminally substituted dihaloC$_1$-C$_6$alkyl group, wherein halo preferably is chloro or bromo, may be converted into compounds wherein L is —CR(ZR$^2$)$_2$ by reaction with a reagent H—Z—R$^2$ or a metal salt thereof, preferably the sodium salt.

If the synthesis of stereochemically pure isomers is intended, stereoselective reaction steps and conditions are recommended. On the other hand conventional methods of separation can be used for obtaining pure isomers from a mixture of stereochemical isomers.

The starting materials of formulae (II), (III) and (IV) for the preparation of the novel compounds of formula (I) are either known or can be obtained by known methods of synthesis.

For example the compounds of formula (II) can be obtained by N-formylating an α-aminoketone or -aldehyde of formula

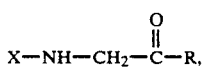   (IX)

wherein R and X are as defined under formula (I), with formic acid in the presence of acetic anhydride. In turn, the compounds of formula (IX) can be prepared by reacting an amine of formula

X—NH$_2$   (X), wherein X is as defined under formula (I), with an α-bromoketone or α-bromoaldehyde of formula

wherein R is as defined under formula (I), in the presence of an acid-binding agent, such as sodium carbonate.

The 4-amino-1H-imidazole derivatives of formula (IV) can be obtained by cyclizing an intermediate of formula

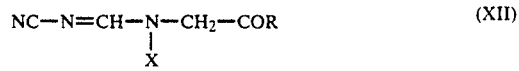

wherein X and R are as defined hereinabove under catalysis of a base at elevated temperature in a suitable solvent, e.g. an alcohol. A preferred mode of carrying out said cyclization may comprise the reaction of the starting compound (XII) in an alcohol in the presence of a catalytic amount of alkoxide obtained by dissolving an alkali metal in said alcohol, at the boiling point of the reaction mixture. Or, alternatively, by reacting (XII) with an alkali metal alkoxide in a polar solvent such as N,N-dimethylformamide or dimethyl sulfoxide. Generally, the reaction temperatures are in the range of +60° C. to +140° C.

The intermediates of formula (XII) in turn can be prepared by alkylating an amidine of formula

NC—N=CH—NH—X   (XIII)

wherein X is as defined under formula (I) with an α-bromoketone or α-bromoaldehyde of formula (XI), in the presence of an appropriate base, such as, for example an alkali metal hydroxide, an alkali or earth alkaline metal carbonate or hydrogen carbonate, an earth alkaline oxide, an alkali metal alkoxide or a trialkylamine, e.g. sodium hydroxide, potassium hydroxide, sodium carbonate, potassium hydrogen carbonate, magnesium oxide, calcium oxide, sodium methoxide, sodium ethoxide, potassium ethoxide, potassium isopropoxide, pyridine, N,N-diethylethanamine and the like. In some instances, the addition of a crown-ether may be recommendable. The reaction may conveniently be conducted at temperatures between +10° C. and the boiling point of the reaction mixture, either without a solvent or in a solvent such as N,N-dimethylformamide, N,N-dimethylacetamide or dimethyl sulfoxide.

The intermediates of formula (XIII) can be prepared by reacting an amine of formula (X) with a C$_1$-C$_5$alkyl-N-cyanomethanimidate of formula C$_1$-C$_5$alkyl—O—CH=N—CN   (XIV)

in an appropriate reaction-inert solvent such as trichloromethane, tetrahydrofuran, 1,4-dioxane, acetonitrile, N,N-dimethylformamide or N,N-dimethylacetamide. The said reaction can conveniently be carried out at temperatures between room temperature and the boiling point of the reaction mixture, in particular between +20° C. and +80° C. Removal of the C$_1$-C$_5$alkanol which is liberated during the course of the reaction and of the solvent by destillation under reduced pressure yields the N-cyanoamidine of formula (XIII) which in general need not be purified before further convertion.

The 4-amino-1H-imidazole derivatives of formula (IV) can alternatively be obtained from the amines of formula (X), by a combined N-alkylating and cyclization reaction in a one-pot procedure. The latter procedure is conducted in the same solvents and bases as mentioned hereinabove for the two step synthesis.

The intermediates of formulae (V), (VII) and (VIII) are known from EP-A-0,207,563, EP-A-0,234,656 and EP-A-0,240,050 and the Brit. Pat. Appl. Nos. 86,30,759, 86,31,019 and 86,31,091.

The compounds of formula (I) are stable compounds and no precautionary measures are required for handling them.

When used at the indicated rates of application, the compounds of formula (I) have good selective herbicidal properties which make them most suitable for use in crops of useful plants, preferably in maize and in rice. In some cases damage is also caused to weeds which up to now have only been controlled with total herbicides.

At higher rates of application, all tested plants are so severely damaged in their development that they die.

The invention also relates to herbicidal compositions containing one or more inert carriers and, if desired, other adjuvants and as active ingredient a herbicidally effective amount of a compound of formula (I) as defined hereinabove. Further the invention relates to methods of controlling weeds by applying thereto or to the locus thereof a herbicidally effective amount of a compound of formula (I) as defined hereinabove.

In the method for controlling weeds according to the invention the compounds of formula (I) are used in unmodified form or, preferably, together with the adjuvants conventionally employed in the art of formulation. They are therefore formulated following art-known procedures to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula (I) and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are aromatic hydrocarbons, preferably the fractions containing 8 to 12 carbon atoms, e.g. dimethylbenzene mixtures or substituted naphthalenes, phthalates such as dibutyl phthalate or dioctyl phthalate, aliphatic or alicyclic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated absorbent carriers are of the porous type, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues.

Depending on the nature of the compound of formula (I) to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, earth alkaline metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. In addition, there may also be mentioned fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, earth alkaline metal salts or unsubstitued or substituted ammonium salts and contain an alkyl radical having from 8 to 22 carbon atoms said alkyl also comprising radicals derived from acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (alifatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxylower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981, M. and J. Ash, "Encyclopedia of Surfactants", Vol. I–III, Chemical Publishing Co., New York, 1980–81.

The herbicidal compositions which are preferably employed in the method of the invention usually contain 0.1 to 95%, preferably 0.1 to 80%, of a compound of formula (I), 1 to 99.9%, of a solid or liquid adjuvant, and 0 to 25%, preferably 0.1 to 25%, of a surfactant.

Preferred compositions are composed in particular of the following constituents (%=percentage by weight):

GEMULSIFIABLE CONCENTRATES
active ingredient: 1 to 20%, preferably 5 to 10%
surfactant: 5 to 30%, preferably 10 to 20%
liquid carrier: 50 to 94%, preferably 70 to 85%

DUSTS
active ingredient: 0.1 to 10%, preferably 0.1 to 1%
solid carrier: 99.9 to 90%, preferably 99.9 to 99%

SUSPENSION CONCENTRATES
active ingredient: 5 to 75%, preferably 10 to 50%
water: 94 to 25%, preferably 88 to 30%
surfactant: 1 to 40%, preferably 2 to 30%

WETTABLE POWDERS
active ingredient: 0.5 to 90%, preferably 1 to 80%
surfactant: 0.5 to 20%, preferably 1 to 15%
solid carrier: 5 to 95%, preferably 15 to 90%

GRANULATES
active ingredient: 0.5 to 30%, preferably 3 to 15%
solid carrier: 99.5 to 70%, preferably 97 to 85%

The following examples are intended to illustrate and not to limit the scope of the present invention. Unless otherwise stated all parts therein are by weight. The preparatory examples show how the novel compounds of formula (I) can be obtained. The biological and formulation examples demonstrate how the novel ingredients can be used as active substances for agrochemical purposes.

EXPERIMENTAL PART

A. Preparation of Final Compounds

Example 1

(a) To a stirred solution of 55 parts of N-(2-oxo-2-phenylethyl)-N-(1,2,3,4-tetrahydro-1-naphthalenyl)formamide in 450 parts of tetrahydrofuran were added portionwise 9.2 parts of a sodium hydride dispersion 50%. Upon complete addition, stirring was continued for 20 minutes at room temperature. After the addition of 50 parts of methyl formate, the whole was stirred overnight at 60° C. (after stirring for 2 hours, another portion of 50 parts of methyl formate was added). After cooling, the reaction mixture was evaporated. The residue was stirred in 500 parts of water and 350 parts of 1,1'-oxybisethane. The separated aqueous layer was acidified with a hydrochloric acid solution and the product was extracted with trichloromethane. The combined organic layers were evaporated and the residue was dissolved in 80 parts of methanol and 80 parts of water. 20 Parts of potassium thiocyanate and 30 parts of concentrated hydrochloric acid were added and the whole was stirred overnight at room temperature. The product was extracted with trichloromethane. The extract was washed with water, dried, filtered and evaporated, yielding 7 parts (11.3%) of [2-mercapto-1-(1,2,3,4-tetrahydro-1-naphthalenyl)-1H-imidazol-5-yl] phenylmethanone as a residue (compound 2.42).

(b) To a stirred solution of 7 parts of [2-mercapto-1-(1,2,3,4-tetrahydro-1-naphthalenyl)-1H-imidazol-5-yl] phenylmethanone in 30 parts of water were added 30 parts of concentrated nitric acid. The whole was stirred for 15 minutes at 50° C. (intense reaction). After cooling, the reaction mixture was poured into crushed ice and treated with a sodium hydroxide solution. The product was extracted with trichloromethane. The extract was washed with water, dried, filtered and evaporated. The residue was converted into the nitrate salt in 1,1'-oxybisethane. The salt was filtered off and dried, yielding 0.9 parts (8.4%) of phenyl [1-(1,2,3,4-tetrahydro-1-naphthalenyl)-1H-imidazol-5-yl]methanone mononitrate; mp. 150.2° C. (compound 2.43).

Example 2

(a) 250 Parts of 2,3-dihydro-2,2-dimethyl-1H-inden-1-amine were dissolved in 80 parts of ethanol. 150 Parts of ethyl-N-cyanoformamidate were added within 10 minutes and the mixture was heated to reflux. The cooled solution was concentrated, the precipitate was filtered off and dried, yielding 316 parts (96%) of N-(2,3-dihydro-2,2-dimethyl-1H-inden-1-yl)-N'-cyanoformamidine; mp. 164°–167° C.

(b) 316 Parts of N-(2,3-dihydro-2,2-dimethyl-1H-inden-1-yl)-N'-cyanoformamidine were suspended in 282 parts of N,N-dimethylformamide. To this suspension were added slowly 163 parts of 2-methyl-2-propanol potassium salt and after stirring at room temperature for 4 hours there were added dropwise 194 parts of bromopropanone. After 48 hours, the reaction mixture was poured into water and extracted with 1,1'-oxybisethane. The separated organic layers were evaporated and the residue was crystallized first from a mixture of 1,1'-oxybisethane and petroleum ether. The precipitate was filtered off and dried and then recrystallized from methylbenzene. The product was filtered off and dried, yielding 93 parts (23%) of [4-amino-1-(2,3-dihydro-2,2-dimethyl-1H-inden-1-yl)-1H-imidazol-5-yl]ethanone; mp. 174°–175° C.

(c) 13 Parts of [5-amino-3-(2,3-dihydro-2,2-dimethyl-1H-inden-1-yl)-1H-imidazol-4-yl]ethanone were dissolved in 167 parts of tetrahydrofuran. To the solution were added dropwise 7.7 parts of 2-methyl-2-propyl nitrite. After stirring at room temperature for 1 hour, the reaction mixture was evaporated to dryness. The residue was purified by column chromatography over silica gel. The pure fractions were collected and the eluent was evaporated. The residue was crystallized from 1,1'-oxybisethane. The product was filtered off and dried, yielding 6.25 parts (51%) of [1-(2,3-dihydro-2,2-dimethyl-1H-inden-1-yl)-1H-imidazol-5-yl]ethanone; mp. 69°–70° C. (compound 1.10).

Example 3

To a stirred solution of 28 parts of methyl (±)-1-(1,2,3,4-tetrahydro-1-naphthalenyl)-1H-imidazole-5-carboxylate in 180 parts of tetrahydrofuran were added 150 parts of a lithium tetrahydroaluminate solution 1M in tetrahydrofuran (exothermic reaction). After stirring for 3 hours, 25 parts of water were added. The reaction mixture was allowed to cool and the precipitate was filtered off. The filtrate was evaporated and the residue was converted into the nitrate salt in 2-propanone and 1,1'-oxybisethane. The salt was filtered off and dried in vacuo, yielding 12.6 parts (43.2%) of 1-(1,2,3,4-tetrahydro-1-naphthalenyl)-1H-imidazole-5-methanol mononitrate; mp. 119.0° C. (compound 2.03).

Example 4

A solution of 8.5 parts of 1-(1,2,3,4-tetrahydro-1-naphthalenyl)-1H-imidazole-5-methanol mononitrate and 17 parts of manganese(IV) oxide in 50 parts of 1,4-dioxane was stirred for 10 hours at 90° C. The reaction mixture was filtered and the filtrate was evaporated. The residue was converted into the nitrate salt in 2-propanone and 2,2'-oxybispropane. The salt was filtered off and dried, yielding 5.9 parts (53.6%) of 1-(1,2,3,4-tetrahydro-1-naphthalenyl)-1H-imidazole-5-carboxaldehyde mononitrate; mp. 161.6° C. (compound 2.05).

Example 5

To a stirred and refluxed Grignard complex, previously prepared starting from 9 parts of bromoethane, 2.16 parts of magnesium and 140 parts of 1,1'-oxybisethane were added dropwise 11.3 parts of 1-(1,2,3,4-tetrahydro-1-naphthalenyl)-1H-imidazole-5-carboxaldehyde. Upon complete addition, stirring was continued for 2 hours at room temperature. The reaction mixture was poured into water and treated with a sodium hydroxide solution. The separated organic layer was washed with water, dried, filtered and evaporated, yielding 4.6 parts (35.8%) of α-ethyl-1-(1,2,3,4-tetrahydro-1-naphthalenyl)-1H-imidazole-5-methanol as a residue (compound 2.06).

Example 6

A solution of 4 parts of α-ethyl-1-(1,2,3,4-tetrahydro-1-naphthalenyl)-1H-imidazole-5-methanol and 8 parts of mangenese(IV) oxide in 50 parts of 1,4-dioxane was stirred for 16 hours at 90° C. The reaction mixture was filtered and the filtrate was evaporated. The residue was converted into the nitrate salt in 2-propanone. The salt was filtered off and purified by column chromatography over silica gel using a mixture of trichloromethane and methanol (90:10 by volume) as eluent. The pure fractions were collected and the eluent was evaporated. The residue was further purified twice by column chromatography (HPLC) over silica gel first using a mixture of ethyl acetate and hexane (90:10 by volume) and then a mixture of tetrachloromethane, trichloromethane and methanol (65:20:15 by volume) as eluents. The pure fractions were collected and the eluent was evaporated. The residue was converted into the nitrate salt in 2-propanone and 2,2'-oxybispropane. The salt was filtered off and dried in vacuo, yielding 0.36 parts (7.0%) of 1-[1-(1,2,3,4-tetrahydro-1-naphthalenyl)-1H-imidazol-5-yl]-1-propanone mononitrate; mp. 140.6° C. (compound 2.07).

Example 7

(a) To a stirred and refluxed solution of 34 parts of methyl (±)-[1α,4α,8aβ]-1-(decahydro-1-naphthalenyl)-1H-imidazole-5-carboxylate in 675 parts of tetrahydrofuran was added dropwise a solution of 75 parts of a sodium dihydrobis(2-methoxyethoxy)aluminate solution 70% in methylbenzene in 135 parts of tetrahydrofuran during 1 hour at reflux temperature. Upon complete addition, stirring was continued for 1 hour at reflux. After cooling in an ice bath, 40 parts of methanol were added dropwise to the reaction mixture. Upon complete addition, 650 parts of water were added. The whole was treated with a sodium hydroxide solution. The separated organic layer was evaporated. The residue was taken up in water and dichloromethane. The dichloromethane layer was dried, filtered and evaporated. The residue was crystallized from acetonitrile. The product was filtered off and dried, yielding 26.3 parts (87.0%) of (±)-[1α,4aα,8aβ]-1-(decahydro-1-naphthalenyl)-1H-imidazole-5-methanol; mp. 130.1° C. (compound 10.01).

(b) A mixture of 23.8 parts of (±)-[1α,4aα,8aβ]-1-(decahydro-1-naphthalenyl)-1H-imidazole-5-methanol, 85 parts of manganese(IV) oxide and 800 parts of 2-propanone was stirred overnight at reflux temperature. The manganese(IV) oxide was filtered off over diatomaceous earth and the filtrate was evaporated. The residue was dissolved in trichloromethane and silica gel was added. After stirring, the whole was filtered over diatomaceous earth. The filtrate was evaporated. The residue was converted into the hydrochloride salt in acetonitrile. The salt was filtered off and dried, yielding 5.55 parts (18.4%) of (±)-[1α,4aα,8aβ]-1-(decahydro-1-naphthalenyl)-1H-imidazole-5-carboxaldehyde monohydrochloride; mp. 212.7° C. (compound 10.02).

(c) A mixture of 12.5 parts of (±)-[1α,4aα,8aβ]-1-(decahydro-1-naphthalenyl)-1H-imidazole-5-carboxaldehyde and 135 parts of tetrahydrofuran was added dropwise to 40 parts of a chloromethyl magnesium solution in tetrahydrofuran 21.8% during 1 hour. Upon complete addition, stirring was continued overnight at room temperature. The reaction mixture was decomposed by the dropwise addition of an aqueous ammonium chloride solution. The separated organic layer was evaporated. The residue was taken up in water and the product was extracted with dichloromethane. The extract was dried, filtered and evaporated. The residue was stirred in 1,1'-oxybisethane. The precipitated product was filtered off and dried, yielding 9.1 parts (67.8%) of (±)-[1α,4aα,8aβ]-1-(decahydro-1-naphthalenyl)-α-methyl-1H-imidazole-5-methanol; mp. 120.9° C. (compound 10.03).

Example 8

A solution of 9.2 parts of α-methyl-1-(1,2,3,4-tetrahydro-1-naphthalenyl)-1H-imidazole-5-methanol and 100 parts of barium manganate in 130 parts of dichloromethane was stirred for 48 hours at room temperature. The reaction mixture was filtered and the filtrate was evaporated. The residue was purified by column chromatography over silica gel using a mixture of trichloromethane and methanol (99:1 by volume) as eluent. The pure fractions were collected and the eluent was evaporated. The residue was converted into the nitrate salt in 2-propanone and 1,1'-oxybisethane. The salt was filtered off and dried, yielding 1.1 parts (9.0%) of 1-[1-(1,2,3,4-tetrahydro-1-naphthalenyl)-1H-imidazol-5-yl]ethanone mononitrate; mp. 165.0° C. (compound 2.08).

Example 9

A solution of 42 parts of chromium(VI) oxide and 66 parts of pyridine in 665 parts of dichloromethane was stirred for 20 minutes at room temperature. A solution of 19 parts of α-ethyl-1-(1,2,3,4-tetrahydro-1-naphthalenyl)-1H-imidazole-5-methanol in 13.3 parts of dichloromethane was added dropwise to the thus obtained mixture. Upon complete addition, stirring was continued for 4 hours at room temperature. The reaction mixture was poured into water and the layers were separated. The organic layer was washed twice with water and evaporated. The residue was purified by column-chromatography over silica gel using a mixture of trichloromethane and methanol (95:5 by volume) as eluent. The pure fractions were collected and the eluent was evaporated. The residue was dried for a long time in vacuo at 100° C., yielding 2.2 parts (12.3%) of 1-[1-(1,2,3,4-tetrahydro-1-naphthalenyl)-1H-imidazol-5-yl]-1-propanone as an oily residue (compound 2.53).

EXAMPLE 10

To a stirred and refluxed Grignard complex, previously prepared starting from 20.9 parts of bromomethane, 4.8 parts of magnesium, 81 parts of methylbenzene, 28.8 parts of tetrahydrofuran and 60.6 parts of N,N-diethylethanamine was added dropwise a solution of 28.4 parts of methyl 1-(1,2,3,4-tetrahydro-2,2-dimethyl-1-naphthalenyl)-1H-imidazole-5-carboxylate in 180 parts of methylbenzene during 1 hour at 5°–10° C. Upon complete addition, stirring was continued for 2 hours at 5°–10° C. The supernatant liquid was removed and water and trichloromethane was added to the remaining residue. The whole was stirred for 15 minutes. The separated organic layer was dried, filtered and evaporated. The oily residue was taken up in 30 parts of a sodium hydroxide solution 50% and 60 parts of water. The mixture was stirred and refluxed for 1 hour. After cooling in an ice bath, dichloromethane was added. The organic layer was washed with water, dried, filtered and evaporated. The residue was purified by column chromatography over silica gel using a mixture of trichloromethane and methanol (95:5 by volume) as eluent. The pure fractions were collected and the eluent was evaporated. The residue was converted into the nitrate salt in 2-propanone and 2,2'-oxybispropane. The salt was filtered off and dried, yielding 7.64 parts (23.0%) of 1-[1-(1,2,3,4-tetrahydro-2,2-dimethyl-1-naphthalenyl)-1H-imidazol-5-yl]ethanone mononitrate; mp. 179.6° C. (compound 2.45).

EXAMPLE 11

A mixture of 25 parts of 1-(1,2,3,4-tetrahydro-2,2-dimethyl-1-naphthalenyl)-1H-imidazole-5-carbonitrile and 360 parts of methanol, saturated with ammonia was hydrogenated at normal pressure and at room temperature with 2 parts of Raney nickel catalyst. After the calculated amount of hydrogen was taken up, the catalyst was filtered off and the filtrate was evaporated. The residue was dried at 100° C., yielding 23 parts (90.0%) of 1-(1,2,3,4-tetrahydro-2,2-dimethyl-1-naphthalenyl)-1H-imidazole-5-methanamine as an oily residue (compound 2.37).

EXAMPLE 12

To a stirred mixture of 5.1 parts of 1-(1,2,3,4-tetrahydro-2,2-dimethyl-1-naphthalenyl)-1H-imidazole-5-methanamine and 75 parts of trichloromethane was added dropwise a solution of 2.0 parts of acetic acid anhydride in 150 parts of trichloromethane. Upon complete addition, stirring was continued for 1 hour at room temperature. The reaction mixture was washed with a sodium carbonate solution 10% and water, dried, filtered and evaporated. The residue was crystallized from 2-propanone. The product was filtered off and dried, yielding 3.61 parts (60.6%) of N-[[1-(1,2,3,4-tetrahydro-2,2-dimethyl-1-naphthalenyl)-1H-imidazol-5-yl]methyl]acetamide; mp. 166.3° C. (compound 2.47).

EXAMPLE 13

To a stirred mixture of 5.1 parts of 1-(1,2,3,4-tetrahydro-2,2-dimethyl-1-naphthalenyl)-1H-imidazole-5-methanamine and 75 parts of trichloromethane were added 1.2 parts of isocyanatomethane. After stirring for 1 hour, the reaction mixture was evaporated. The residue was purified by column chromatography over silica gel using a mixture of trichloromethane and methanol (95:5 by volume) as eluent. The pure fractions were collected and the eluent was evaporated. The residue was crystallized from 4-methyl-2-pentanone and 2,2'-oxybispropane. The product was filtered off and dried, yielding 2.9 parts (46.4%) of N-[[1-(1,2,3,4-tetrahydro-2,2-dimethyl-1-naphthalenyl)-1H-imidazol-5-yl]methyl]-N'-methylurea; mp. 120.1° C. (compound 2.54).

EXAMPLE 14

A mixture of 4.04 parts 1-(1-phenylethyl)-1H-imidazole-5-methanol, 30 parts of glacial acetic acid and 2.5 parts of propanoic acid anhydride was refluxed for 2 hours. After keeping at room temperature for 36 hours, the reaction mixture was evaporated. Water was added to the residue and the solution was alkalized by addition of solid sodium bicarbonate. The mixture was extracted with 1,1'-oxybisethane. The extract was dried and 2-propanol, previously saturated with gaseous hydrogen chloride was added to it. The precipitated hydrochloride was filtered off, yielding 4.8 parts of [1-(1-phenylethyl)-1H-imidazol-5-yl]methyl acetate monohydrochloride; mp. 176°–177° C. (compound 8.36).

EXAMPLE 15

A solution of 2 parts of 1-(3,4-dihydro-2,2-dimethyl-2H-1-benzopyran-4-yl)-1H-imidazole-5-methanol and 1 part of acetic acid anhydride in 30 parts of pyridine was stirred for 1 hour at room temperature. The pyridine layer was evaporated and the residue was taken up in 1,1'-oxybisethane. The organic layer was washed three times with water, dried, filtered and evaporated. The residue was converted into the nitrate salt in 1,1'-oxybisethane. The salt was filtered off and dried in vacuo, yielding 1.9 parts (65.3%) of 1-(3,4-dihydro-2,2-dimethyl-2H-1-benzopyran-4-yl)-1H-imidazole-5-methanol acetate(ester) mononitrate; mp. 150.3° C. (compound 6.05).

EXAMPLE 16

3 Parts of 1-(1-phenylethyl)-1H-imidazole-5-methanol monohydrochloride were added portionwise to 16 parts of thionyl chloride (exothermic reaction with evolution of SO₂/HCl). After the addition was complete, the whole was stirred and refluxed for 30 minutes. After cooling there were added 40 parts of 2-propanol, whereupon a solid was precipitated. It was filtered off and recrystallized from a mixture of 60 parts of 2-propanol and 60 parts of 2,2'-oxybispropane, yielding 1.5 parts of 5-(chloromethyl)-1-(1-phenylethyl)-1H-imidazole monohydrochloride; mp. 173.5°–175° C. (dec.) (compound 8.49).

EXAMPLE 17

Through a stirred mixture of 3 parts of 5-(chloromethyl)-1-(1-phenylethyl)-1H-imidazole monohydrochloride and 45 parts of N,N-dimethylformamide were bubbled 3 equivalents of gaseous methanamine at room temperature during a 1 hour-period: exothermic reaction, the temperature rose to 50° C. The reaction mixture was taken up in trichloromethane and methanol, previously saturated with ammonia, was added. The formed precipitate was filtered off and the filtrate was purified by column chromatography over silica gel using a mixture of trichloromethane and methanol, saturated with ammonia, (90:10 by volume) as eluent. The pure fractions were collected and the eluent was evaporated. The residue was converted into the hydrochloride salt in 2-propanol. The salt was filtered off, washed with 2-propanol, dried and crystallized from 2-propanol, yielding 1.6 parts (44.5%) of (±)-N-methyl-1-(1-phenylethyl)-1H-imidazole-5-methanamine dihydrochloride.monohydrate; mp. 109° C. (compound 8.38).

EXAMPLE 18

To a stirred solution of 1.38 parts of sodium in 40 parts of methanol were added 3.84 parts of 5-(chloromethyl)-1-(1-phenylethyl)-1H-imidazole monohydrochloride. Stirring was continued for one hour at reflux. The reaction mixture was evaporated. Water was added to the residue and the product was extracted with 2,2'-oxybispropane. The extract was dried, filtered and evaporated. The residue was purified by column chromatography over silica gel using a mixture of trichloromethane and methanol (98.5:1.5 by volume) as eluent. The pure fractions were collected and the eluent was evaporated. The residue was converted into the hydrochloride salt in 4-methyl-2-pentanone. The salt was filtered off and dried, yielding 1.8 parts of 5-(methoxymethyl)-1-(1-phenylethyl)-1H-imidazole monohydrochloride; mp. 166.3° C. (compound 8.37).

EXAMPLE 19

To a stirred mixture of 5.1 parts of 1-(1,2,3,4-tetrahydro-2,2-dimethyl-1-naphthalenyl)-1H-imidazole-5-carboxaldehyde, 2.7 parts of 1,2-ethanethiol and 130 parts of dichloromethane were added dropwise 9.6 parts of chlorotrimethylsilane. Upon complete addition, stirring was continued overnight at 40° C. After cooling, the reaction mixture was washed with a potassium carbonate solution 10% in water and water, dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2,2'-oxybispropane. The product was filtered off and dried, yielding 3.69 parts (55.8%) of 5-(1,3-dithiolan-2-yl)-1-(1,2,3,4-tetrahydro-2,2-dimethyl-1-naphthalenyl)-1H-imidazole; mp. 109.3° C. (compound 2.52).

EXAMPLE 20

A mixture of 3.8 parts of 1-(1,2,3,4-tetrahydro-2,2-dimethyl-1-naphthalenyl)-1H-imidazole-5-carboxaldehyde, 2.07 parts of hydroxylamine hydrochloride and 50 parts of pyridine was stirred overnight at reflux temperature. The reaction mixture was evaporated and the residue was taken up in water. The product was extracted with trichloromethane. The extract was dried, filtered and evaporated. The residue was crystallized from ethanol. The product was filtered off and dried, yielding 2.1 parts (51.9%) of (E+Z)-1-(1,2,3,4-tetrahydro-2,2-dimethyl-1-naphthalenyl)-1H-imidazole-5-carboxaldehyde,oxime; mp. 213.9° C. (compound 2.49).

EXAMPLE 21

To a stirred solution of 2.1 parts of 1-(2,2-dimethyl-1,2,3,4-tetrahydro-1-naphthalenyl)-1H-imidazole-5-carboxyaldehyde in 11.3 parts of dichloromethane were added 1.8 parts of diethylaminosulfur trifluoride and the reaction mixture was refluxed for 48 hours. An additional 2.0 parts of diethylaminosulfur trifluoride were added and the refluxing was continued for another 48 hours. 1.5 Parts of more diethylaminosulfur trifluoride were added and the mixture was refluxed during 96 hours. The reaction mixture was poured into ice-water. The organic phase was separated and the aqueous layer was extracted twice with dichloromethane. The combined organic extracts were washed with sodium hydrogen carbonate and water, dried with sodium sulfate, filtered and concentrated under reduced pressure. The residue was purified by flash chromatography over silica gel using a mixture of 1,1'-oxybisethane and dichloromethane (1:3 by volume) as eluent. The pure fractions were collected and the eluent was evaporated, yielding 1.2 parts (52.6%) of 5-(difluoromethyl)-1-(2,2-dimethyl-1,2,3,4-tetrahydro-1-naphthalenyl)-1H-imidazole (compound 2.61) as an oily residue, containing approximately 5% of the starting material. The thus obtained oil slowly crystallized upon standing.

Elementary analysis: Calculated: C, 69.54%; H, 6.5%; N, 10.14%; F, 13.7% Found: C, 69.4%; H, 6.6%; N, 10.3%; F, 12.8%.

All other compounds listed in tables 1 to 21 can be obtained by analogous methods of preparation.

TABLE 1

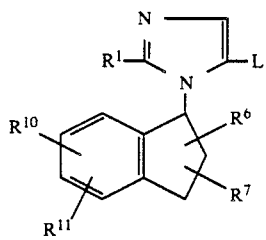

| Comp. No. | $R^1$ | $R^6$ | $R^7$ | $R^{10}$ | $R^{11}$ | L | Phys. data |
|---|---|---|---|---|---|---|---|
| 1.01 | H | 2-CH$_3$ | 2-CH$_3$ | H | H | —CH$_2$OH | |
| 1.02 | H | 2-CH$_3$ | 2-CH$_3$ | H | H | —CH$_2$O—CO—CH$_3$ | |
| 1.03 | H | 2-CH$_3$ | 2-CH$_3$ | H | H | —CH$_2$O—CH$_3$ | |
| 1.04 | H | 2-CH$_3$ | 2-CH$_3$ | H | H | —CH$_2$O—CO—C$_6$H$_5$ | |
| 1.05 | H | 2-CH$_3$ | 2-CH$_3$ | H | H | —CH$_2$O—C$_6$H$_5$ | |
| 1.06 | H | 2-CH$_3$ | 2-CH$_3$ | H | H | —COH | |
| 1.07 | H | 2-CH$_3$ | 2-CH$_3$ | H | H | $\underset{O\diagdown\;\;\diagup O}{\overset{\diagup C\diagdown C_2H_5}{\phantom{x}}}$ (cyclic) | |
| 1.08 | H | 2-CH$_3$ | 2-CH$_3$ | H | H | —CH(OH)C$_2$H$_5$ | |
| 1.09 | H | 2-CH$_3$ | 2-CH$_3$ | H | H | —CO—C$_2$H$_5$ | |
| 1.10 | H | 2-CH$_3$ | 2-CH$_3$ | H | H | —CO—CH$_3$ | mp.68–70° C. |
| 1.11 | H | 2-CH$_3$ | 2-CH$_3$ | H | H | —CO—C$_3$H$_7$-n | |
| 1.12 | H | 2-CH$_3$ | 2-CH$_3$ | H | H | —C(=NOCH$_3$)C$_2$H$_5$ | |
| 1.13 | H | 2-CH$_3$ | 2-CH$_3$ | H | H | —C(=NOH)C$_2$H$_5$ | |
| 1.14 | H | 2-CH$_3$ | 2-CH$_3$ | H | H | —CS—C$_2$H$_5$ | |
| 1.15 | H | 2-CH$_3$ | H | H | H | —CH$_2$—OH | |
| 1.16 | H | 2-CH$_3$ | H | H | H | —CO—C$_2$H$_5$ | |
| 1.17 | H | 2-CH$_3$ | H | H | H | —CO—CH$_3$ | |
| 1.18 | H | 2-CH$_3$ | H | H | H | —CH$_2$—O—CH$_3$ | |
| 1.19 | H | 2-CH$_3$ | H | H | H | —CH$_2$—O—CO—CH$_3$ | |
| 1.20 | H | 2-CH$_3$ | H | H | H | —COH | |
| 1.21 | H | 2-CH$_3$ | H | 5-CH$_3$ | 7-CH$_3$ | —CO—C$_2$H$_5$ | |
| 1.22 | H | 2-(CH$_2$)$_4$-2 | | H | H | —COH | |
| 1.23 | H | 2-(CH$_2$)$_4$-2 | | H | H | —CO—C$_2$H$_5$ | |
| 1.24 | H | 2-C$_2$H$_5$ | 2-C$_2$H$_5$ | H | H | —CO—C$_2$H$_5$ | |
| 1.25 | H | 2-CH$_3$ | 2-C$_2$H$_5$ | H | H | —CH$_2$—OH | |
| 1.26 | H | 2-CH$_3$ | 2-C$_2$H$_5$ | H | H | —COH | |
| 1.27 | H | 2-CH$_3$ | 2-C$_2$H$_5$ | H | H | —CO—C$_2$H$_5$ | |
| 1.28 | H | 2-CH$_3$ | 2-C$_2$H$_5$ | H | H | —CH$_2$—O—CH$_3$ | |
| 1.29 | H | 2-CH$_3$ | 2-C$_2$H$_5$ | H | H | —CO—CH$_3$ | |
| 1.30 | H | H | H | H | H | —CO—C$_2$H$_5$ | |
| 1.31 | H | 3-CH$_3$ | 3-CH$_3$ | H | H | —CO—C$_2$H$_5$ | |
| 1.32 | H | 3-CH$_3$ | 3-CH$_3$ | H | H | —COH | |
| 1.33 | H | 2-CH$_3$ | 3-CH$_3$ | H | H | —CO—C$_2$H$_5$ | |
| 1.34 | H | 2-CH$_3$ | 3-CH$_3$ | H | H | —COH | |
| 1.35 | H | 2-CH$_3$ | 3-CH$_3$ | H | H | —CH$_2$—OH | |
| 1.36 | H | 3-CH$_3$ | 3-CH$_3$ | H | H | —CH$_2$—OH | |
| 1.37 | SH | 2-(CH$_2$)$_3$-3 | | H | H | —CH$_2$—OH | |
| 1.38 | H | 2-(CH$_2$)$_3$-3 | | H | H | —COH | |
| 1.39 | SH | 2-(CH$_2$)$_4$-3 | | H | H | —CO—C$_2$H$_5$ | |
| 1.40 | H | 2-(CH$_2$)$_4$-3 | | H | H | —CO—CH$_3$ | |
| 1.41 | H | 2-C$_2$H$_5$ | 2-C$_2$H$_5$ | H | H | —CH$_2$—OH | |
| 1.42 | H | 2-C$_2$H$_5$ | 2-C$_2$H$_5$ | H | H | —COH | |
| 1.43 | H | 2-C$_2$H$_5$ | 2-C$_2$H$_5$ | H | H | —CO—CH$_3$ | |
| 1.44 | H | 2-C$_2$H$_5$ | 2-C$_2$H$_5$ | H | H | —CH$_2$—O—CH$_3$ | |
| 1.45 | H | 2-C$_2$H$_5$ | 2-C$_2$H$_5$ | H | H | —CH$_2$—O—CO—CH$_3$ | |
| 1.46 | H | 2-C$_2$H$_5$ | 2-C$_2$H$_5$ | H | H | $\underset{O\diagdown\;\;\diagup O}{\overset{\diagup C\diagdown C_2H_5}{\phantom{x}}}$ (cyclic) | |
| 1.47 | H | 2-CH$_3$ | 2-CH$_3$ | 6-CH$_3$ | H | —CO—C$_2$H$_5$ | |
| 1.48 | H | 2-CH$_3$ | 2-CH$_3$ | 6-F | H | —CO—C$_2$H$_5$ | |
| 1.49 | H | 2-CH$_3$ | 2-CH$_3$ | 6-OCH$_3$ | H | —CO—C$_2$H$_5$ | |
| 1.50 | H | 2-CH$_3$ | 2-CH$_3$ | 6-Br | H | —CO—C$_2$H$_5$ | |
| 1.51 | SH | 2-CH$_3$ | 2-CH$_3$ | 6-Br | H | —CO—C$_2$H$_5$ | |
| 1.52 | H | 2-CH$_3$ | 2-CH$_3$ | 5-F | H | —CO—C$_2$H$_5$ | |
| 1.53 | H | 2-CH$_3$ | 2-CH$_3$ | 5-CH$_3$ | H | —CO—C$_2$H$_5$ | |
| 1.54 | H | 2-(CH$_2$)$_5$-2 | | H | H | —CO—C$_2$H$_5$ | |
| 1.55 | SH | 2-(CH$_2$)$_5$-2 | | H | H | —CO—C$_2$H$_5$ | |
| 1.56 | H | 2-CH$_3$ | 2-CH$_3$ | H | H | —CH$_2$—S—CH$_3$ | |
| 1.57 | H | 2-CH$_3$ | 2-CH$_3$ | 6-CH$_3$ | H | —COH | |

TABLE 1-continued

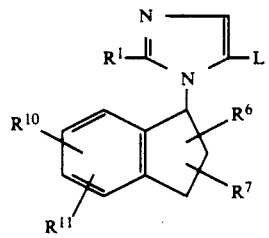

| Comp. No. | $R^1$ | $R^6$ | $R^7$ | $R^{10}$ | $R^{11}$ | L | Phys. data |
|---|---|---|---|---|---|---|---|
| 1.58 | SH | 2-CH$_3$ | 2-CH$_3$ | H | H | —CO—C$_2$H$_5$ | |
| 1.59 | H | 2-CH$_3$ | 2-CH$_3$ | 6-CH$_3$ | H | —CH$_2$—OH | |
| 1.60 | H | 2-CH$_3$ | 2-CH$_3$ | 6-F | H | —COH | |
| 1.61 | H | 2-CH$_3$ | 2-CH$_3$ | 6-F | H | —CH$_2$—OH | |
| 1.62 | H | 2-CH$_3$ | 2-CH$_3$ | 6-Br | H | —CHO | |
| 1.63 | H | 2-CH$_3$ | 2-CH$_3$ | 6-Br | H | —CH$_2$—OH | |
| 1.64 | H | 2-CH$_3$ | 2-CH$_3$ | 5-F | H | —COH | |
| 1.65 | H | 2-CH$_3$ | 2-CH$_3$ | 5-F | H | —CH$_2$—OH | |
| 1.66 | H | 2-CH$_3$ | 2-CH$_3$ | 5-CH$_3$ | H | —CO—CH$_3$ | |
| 1.67 | H | 2-CH$_3$ | 2-CH$_3$ | H | H | —CH$_2$—N(CH$_3$)$_2$ | |
| 1.68 | H | 2-CH$_3$ | 2-CH$_3$ | H | H | —CH$_2$—NH$_2$ | |
| 1.69 | H | 2-CH$_3$ | 2-CH$_3$ | H | H | —CO—CF$_3$ | |
| 1.70 | H | 2-CH$_3$ | 2-CH$_3$ | H | H | —CO—C$_2$F$_5$ | |
| 1.71 | H | 2-CH$_3$ | 2-CH$_3$ | H | H | —HC(OH)—CF$_3$ | |
| 1.72 | H | 2-CH$_3$ | 2-CH$_3$ | H | H | —HC(OH)—C$_2$F$_5$ | |
| 1.73 | SH | 2-CH$_3$ | 2-CH$_3$ | H | H | —CO—C$_6$H$_5$ | |
| 1.74 | H | 2-CH$_3$ | 2-CH$_3$ | H | H | —CO—C$_6$H$_5$ | |
| 1.75 | H | 2-CH$_3$ | 2-CH$_3$ | H | H | —CO—CH(CH$_3$)—C$_3$H$_7$-n | oil |
| 1.76 | H | 2-CH$_3$ | 2-CH$_3$ | H | H | —CH$_2$Cl | |
| 1.77 | H | 2-CH$_3$ | 2-CH$_3$ | H | H | —CH$_2$Br | |
| 1.78 | H | 2-CH$_3$ | 2-CH$_3$ | H | H | —CH$_2$F | |
| 1.79 | H | 2-CH$_3$ | 2-CH$_3$ | H | H | —CHF$_2$ | |
| 1.80 | H | 2-CH$_3$ | 2-CH$_3$ | H | H | —CF$_3$ | |
| 1.81 | H | 2-CH$_3$ | 2-CH$_3$ | H | H | —CCl$_3$ | |

TABLE 2

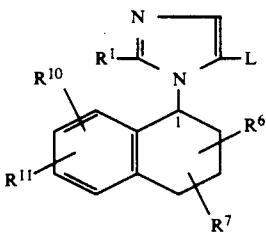

| Comp. No. | $R^1$ | $R^6$ | $R^7$ | $R^{10}$ | $R^{11}$ | L | Physical data |
|---|---|---|---|---|---|---|---|
| 2.01 | H | H | H | 6-Cl | H | —CH$_2$OH | |
| 2.02 | H | H | H | 7-F | H | —CH$_2$OH | |
| 2.03 | H | H | H | H | H | —CH$_2$OH | .HNO$_3$/mp. 119.0° C. |
| 2.04 | H | 2-CH$_3$ | 2-CH$_3$ | H | H | —CH$_2$OH | mp. 159.4° C. |
| 2.05 | H | H | H | H | H | —COH | .HNO$_3$/mp. 161.6° C. |
| 2.06 | H | H | H | H | H | —CH(OH)—C$_2$H$_5$ | mp. 122.8° C. |
| 2.07 | H | H | H | H | H | —CO—C$_2$H$_5$ | .HNO$_3$/mp. 140.6° C. |
| 2.08 | H | H | H | H | H | —CO—CH$_3$ | .HNO$_3$/mp. 165° C. |
| 2.09 | H | H | H | H | H | —CH$_2$—O—CH$_3$ | |
| 2.10 | H | 2-CH$_3$ | 2-CH$_3$ | H | H | —COH | mp. 138.6° C. |
| 2.11 | H | 2-CH$_3$ | 2-CH$_3$ | H | H | —CH(OH)—C$_2$H$_5$ | |
| 2.12 | H | 2-CH$_3$ | 2-CH$_3$ | H | H | —CO—C$_2$H$_5$ | HNO$_3$/mp. 161.2° C. |
| 2.13 | H | 2-CH$_3$ | 2-CH$_3$ | H | H | —CH$_2$—O—CH$_3$ | HNO$_3$/mp. 150.6° C. |
| 2.14 | H | 2-CH$_3$ | 2-CH$_3$ | H | H | —CH$_2$—O—CO—CH$_3$ | HNO$_3$/mp. 141.6° C. |
| 2.15 | H | 2-CH$_3$ | H | H | H | —CH$_2$—OH | trans |
| 2.16 | H | 2-CH$_3$ | H | H | H | —CO—C$_2$H$_5$ | |
| 2.17 | H | 2-CH$_3$ | H | H | H | —COH | |
| 2.18 | H | 2-(CH$_2$)$_4$-2 | | H | H | —CH$_2$—OH | |
| 2.19 | H | 2-(CH$_2$)$_4$-2 | | H | H | —COH | |
| 2.20 | H | 2-(CH$_2$)$_4$-2 | | H | H | —CO—C$_2$H$_5$ | |
| 2.21 | H | 2-(CH$_2$)$_4$-2 | | H | H | —CH(OH)—C$_2$H$_5$ | |

TABLE 2-continued

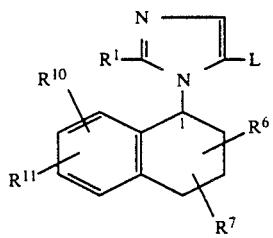

| Comp. No. | R¹ | R⁶ | R⁷ | R¹⁰ | R¹¹ | L | Physical data |
|---|---|---|---|---|---|---|---|
| 2.22 | H | 2-(CH₂)₄-2 | | H | H | —CH₂—O—CH₃ | |
| 2.23 | H | 2-(CH₂)₅-2 | | H | H | —CH₂—OH | |
| 2.24 | H | 2-(CH₂)₅-2 | | H | H | —COH | |
| 2.25 | H | 2-(CH₂)₅-2 | | H | H | —CO—C₂H₅ | |
| 2.26 | H | 2-(CH₂)₅-2 | | H | H | —CH(OH)—C₂H₅ | |
| 2.27 | H | 2-(CH₂)₅-2 | | H | H | —CH₂—O—CH₃ | |
| 2.28 | H | 2-C₂H₅ | H | H | H | —CH₂—OH | |
| 2.29 | H | 2-C₃H₇-n | H | H | H | —CH₂—OH | |
| 2.30 | H | 2-C₄H₉-n | H | H | H | —CH₂—OH | |
| 2.31 | H | 2-C₅H₁₁-n | H | H | H | —CH₂—OH | |
| 2.32 | H | 2-C₃H₇-i | H | H | H | —CH₂—OH | |
| 2.33 | H | 2-(CH₂)₃-3 | | H | H | —CH₂—OH | |
| 2.34 | H | 3-(CH₂)₃-4 | | H | H | —CO—C₂H₅ | |
| 2.35 | H | 2-(CH₂)₄-3 | | H | H | —CO—C₂H₅ | |
| 2.36 | H | 2-CH₃ | 2-CH₃ | H | H | —CH₂—N(CH₃)₂ | |
| 2.37 | H | 2-CH₃ | 2-CH₃ | H | H | —CH₂—NH₂ | oil |
| 2.38 | H | 2-CH₃ | 2-CH₃ | H | H | —CO—CF₃ | |
| 2.39 | H | 2-CH₃ | 2-CH₃ | H | H | —CO—C₂F₅ | |
| 2.40 | H | 2-CH₃ | 2-CH₃ | H | H | —CH(OH)—CF₃ | |
| 2.41 | H | 2-CH₃ | 2-CH₃ | H | H | —CH(OH)—C₂F₅ | |
| 2.42 | SH | H | H | H | H | —CO—C₆H₅ | solid residue |
| 2.43 | H | H | H | H | H | —CO—C₆H₅ | HNO₃/mp. 150.2° C. |
| 2.44 | H | H | H | H | H | —CH(OH)CH₃ | solid residue |
| 2.45 | H | 2-CH₃ | 2-CH₃ | H | H | —CO—CH₃ | HNO₃/mp. 179.6° C. |
| 2.46 | H | 2-CH₃ | 2-CH₃ | H | H | —CO—C₃H₇-n | HNO₃/mp. 148.1° C. |
| 2.47 | H | 2-CH₃ | 2-CH₃ | H | H | —CH₂—NH—CO—CH₃ | mp. 166.3° C. |
| 2.48 | H | 2-CH₃ | 2-CH₃ | H | H | —CH(OH)—CH₃ | mp. 176.7° C. |
| 2.49 | H | 2-CH₃ | 2-CH₃ | H | H | —CH=N—OH | (E + Z)/mp. 213.9° C. |
| 2.50 | H | 2-CH₃ | 2-CH₃ | H | H | —CH=N—O—CH₃ | (E + Z)/mp. 166.1° C. |
| 2.51 | H | 2-CH₃ | 2-CH₃ | H | H | (1,3-dioxolan-2-yl with 2-CH₃) | HNO₃/mp. 173.5° C. |
| 2.52 | H | 2-CH₃ | 2-CH₃ | H | H | (1,3-dithiolan-2-yl with 2-CH₃) | mp. 109.3° C. |
| 2.53 | H | H | H | H | H | —CO—CH₂—CH₃ | oil |
| 2.54 | H | 2-CH₃ | 2-CH₃ | H | H | —CH₂NHCONHCH₃ | mp. 120.1° C. |
| 2.55 | H | H | H | H | H | —CH₂—O—CO—CH₃ | resin |
| 2.56 | H | 2-CH₃ | 2-CH₃ | H | H | —C(=N—OH)CH₃ | (E + Z)/mp. 263.6° C. |
| 2.57 | H | 2-CH₃ | 2-CH₃ | H | H | —C(=N—OCH₃)CH₃ | (E + Z)/mp. 83.6° C. |
| 2.58 | H | 2-CH₃ | 2-CH₃ | H | H | —CH₂Cl | HCl/½H₂O mp. 130° C. |
| 2.59 | H | 2-CH₃ | 2-CH₃ | H | H | —CH₂Br | |
| 2.60 | H | 2-CH₃ | 2-CH₃ | H | H | —CH₂F | |
| 2.61 | H | 2-CH₃ | 2-CH₃ | H | H | —CHF₂ | oil |
| 2.62 | H | 2-CH₃ | 2-CH₃ | H | H | —CF₃ | |
| 2.63 | H | 2-CH₃ | 2-CH₃ | H | H | —CCl₃ | |

TABLE 3

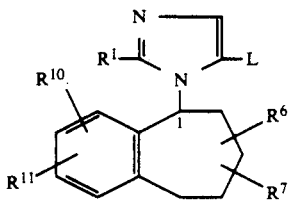

| Comp. No. | $R^1$ | $R^6$ | $R^7$ | $R^{10}$ | $R^{11}$ | L | Physical data |
|---|---|---|---|---|---|---|---|
| 3.01 | H | H | H | H | H | —CH$_2$OH | |
| 3.02 | H | H | H | H | H | —COH | |
| 3.03 | H | H | H | H | H | —CO—C$_2$H$_5$ | |
| 3.04 | H | H | H | H | H | —CH$_2$—O—CH$_3$ | |
| 3.05 | H | H | H | H | H | —CH(OH)—C$_2$H$_5$ | |
| 3.06 | H | H | H | H | H | —CHF$_2$ | |

TABLE 4

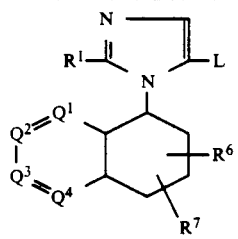

| Comp. No. | $R^1$ | $R^6$ | $R^7$ | $Q^1=Q^2-Q^3=Q^4$ | L | Physical data |
|---|---|---|---|---|---|---|
| 4.01 | H | H | H | CH=CH—CH=N | —CH$_2$OH | |
| 4.02 | H | H | H | CH=CH—CH=N | —COH | |
| 4.03 | H | H | H | CH=CH—N=CH | —CH$_2$OH | |
| 4.04 | H | H | H | CH=CH—N=CH | —COH | |
| 4.05 | H | H | H | CH=N—CH=CH | —CH$_2$OH | |
| 4.06 | H | H | H | CH=N—CH=CH | —COH | |
| 4.07 | H | H | H | N=CH—CH=CH | —CH$_2$OH | |
| 4.08 | H | H | H | N=CH—CH=CH | —COH | |
| 4.09 | H | H | H | CH=CH—CH=N | —CH$_2$Cl | |
| 4.10 | H | H | H | CH=CH—CH=N | —CHF$_2$ | |
| 4.11 | H | H | H | N=CH—CH=CH | —CH$_2$F | |

TABLE 4-continued

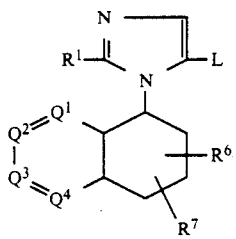

| Comp. No. | $R^1$ | $R^6$ | $R^7$ | $Q^1=Q^2-Q^3=Q^4$ | L | Physical data |
|---|---|---|---|---|---|---|
| 4.12 | H | H | H | N=CH—CH=CH | —CHF$_2$ | |

TABLE 5

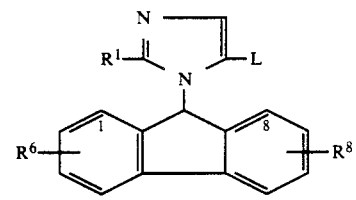

| Comp. No. | $R^1$ | $R^6$ | $R^8$ | L | Physical data |
|---|---|---|---|---|---|
| 5.01 | H | H | H | —CH$_2$OH | |
| 5.02 | SH | H | H | —CH$_2$OH | |
| 5.03 | H | H | H | —COH | |
| 5.04 | SH | H | H | —COH | |
| 5.05 | H | H | H | —CO—C$_2$H$_5$ | |
| 5.06 | SH | H | H | —CO—C$_2$H$_5$ | |
| 5.07 | H | H | H | —CH(OH)—C$_2$H$_5$ | |
| 5.08 | H | H | H | —CH$_2$—O—CH$_3$ | |
| 5.09 | H | 1-CH$_3$ | H | —CH$_2$OH | |
| 5.10 | H | 1-CH$_3$ | 8-CH$_3$ | —CH$_2$OH | |
| 5.11 | H | H | H | —CH$_2$Cl | |
| 5.12 | H | H | H | —CH$_2$F | |
| 5.13 | H | H | H | —CHF$_2$ | |
| 5.14 | H | H | H | —CF$_3$ | |
| 5.15 | H | H | H | —CCl$_3$ | |

TABLE 6

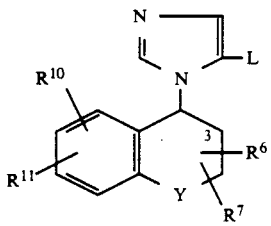

| Comp. No. | Y | $R^6$ | $R^7$ | $R^{10}$ | $R^{11}$ | L | Physical data |
|---|---|---|---|---|---|---|---|
| 6.01 | O | 2-CH$_3$ | 2-CH$_3$ | H | H | —CH$_2$OH | mp. 163.4° C. |
| 6.02 | O | 2-CH$_3$ | 2-CH$_3$ | H | H | —COH | HNO$_3$/mp. 154.2° C. |
| 6.03 | O | 2-CH$_3$ | 2-CH$_3$ | H | H | —CO—C$_2$H$_5$ | |
| 6.04 | O | 2-CH$_3$ | 2-CH$_3$ | H | H | —CH(OH)—C$_2$H$_5$ | |
| 6.05 | O | 2-CH$_3$ | 2-CH$_3$ | H | H | —CH—O—CO—CH$_3$ | HNO$_3$/mp. 150.3° C. |
| 6.06 | O | 2-CH$_3$ | 2-CH$_3$ | H | H | —CH$_2$—O—CH$_3$ | |
| 6.07 | O | 2-CH$_3$ | H | H | H | —CH$_2$OH | trans |
| 6.08 | O | 2-CH$_3$ | H | H | H | —COH | trans |
| 6.09 | O | 2-CH$_3$ | H | H | H | —CO—C$_2$H$_5$ | trans |
| 6.10 | O | 2-CH$_3$ | H | H | H | 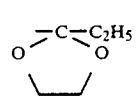 | trans |
| 6.11 | O | 2-CH$_3$ | H | H | H | —CH$_2$—O—CH$_3$ | trans |

TABLE 6-continued

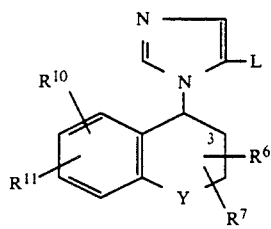

| Comp. No. | Y | $R^6$ | $R^7$ | $R^{10}$ | $R^{11}$ | L | Physical data |
|---|---|---|---|---|---|---|---|
| 6.12 | O | 2-$CH_3$ | H | H | H | —$CH_2OH$ | cis |
| 6.13 | O | 2-$CH_3$ | H | H | H | —COH | cis |
| 6.14 | O | 3-$CH_3$ | H | H | H | —$CH_2OH$ | trans |
| 6.15 | O | 3-$CH_3$ | H | H | H | —COH | trans |
| 6.16 | O | H | H | H | H | —$CH_2OH$ | |
| 6.17 | O | 2-$(CH_2)_4$-3 | | H | H | —$CH_2OH$ | |
| 6.18 | O | 2-$(CH_2)_4$-3 | | H | 6-Br | —$CH_2OH$ | |
| 6.19 | O | 2-$(CH_2)_3$-3 | | H | H | —$CH_2OH$ | |
| 6.20 | O | 2-$CH_3$ | H | H | H | —CO—$C_2H_5$ | trans |
| 6.21 | O | 2-$CH_3$ | H | H | H | —CH(OH)—$C_2H_5$ | trans |
| 6.22 | O | 2-$CH_3$ | H | H | H | —CO—$CH_3$ | trans |
| 6.23 | O | 2-$CH_3$ | 2-$CH_3$ | H | H | —CH(OH)$CH_3$ | oil |
| 6.24 | O | 2-$CH_3$ | 2-$CH_3$ | H | H | —CO—$CH_3$ | $HNO_3$/mp. 150.5° C. |
| 6.25 | O | 2-$CH_3$ | 3-$CH_3$ | H | H | —$CH_2$—OH | (±)-(2α,3α,4β)/solid |
| 6.26 | O | 2-$CH_3$ | 3-$CH_3$ | H | H | —CHO | (±)-(2α,3α,4β) mp. 152.7° C. |
| 6.27 | O | 2-$CH_3$ | 3-$CH_3$ | H | H | —CH(OH)—$CH_3$ | (±)-(2α,3α,4β) mp. 136.3° C. |
| 6.28 | O | 2-$CH_3$ | 3-$CH_3$ | H | H | —CO—$CH_3$ | (±)-(2α,3α,4β) $HNO_3$/mp. 171.5° C. |
| 6.29 | O | 3-$CH_3$ | 3-$CH_3$ | H | H | —$CH_2Cl$ | |
| 6.30 | O | 3-$CH_3$ | 3-$CH_3$ | H | H | —$CH_2F$ | |
| 6.31 | O | 3-$CH_3$ | 3-$CH_3$ | H | H | —$CH_2Br$ | |
| 6.32 | O | 3-$CH_3$ | 3-$CH_3$ | H | H | —$CH_2I$ | |
| 6.33 | O | 3-$CH_3$ | 3-$CH_3$ | H | H | —$CHF_2$ | |
| 6.34 | O | 3-$CH_3$ | 3-$CH_3$ | H | H | —$CF_3$ | |
| 6.35 | O | 3-$CH_3$ | 3-$CH_3$ | H | H | —$CCl_3$ | |
| 6.36 | O | 3-$CH_3$ | 3-$CH_3$ | H | H | —$CF_2$—$CH_3$ | |
| 6.37 | O | 3-$CH_3$ | 3-$CH_3$ | H | H | —CHCl—$CH_3$ | |
| 6.38 | O | 3-$CH_3$ | 3-$CH_3$ | H | H | —CHF—$CH_3$ | |
| 6.39 | O | 2-$CH_3$ | 2-$CH_3$ | H | H | —$CH_2Cl$ | |
| 6.40 | O | 2-$CH_3$ | 2-$CH_3$ | H | H | —$CH_2F$ | |
| 6.41 | O | 2-$CH_3$ | 2-$CH_3$ | H | H | —$CHF_2$ | |
| 6.42 | O | 2-$CH_3$ | 2-$CH_3$ | H | H | —$CF_3$ | |
| 6.43 | O | 2-$CH_3$ | 2-$CH_3$ | H | H | —CHCl—$CH_3$ | |
| 6.44 | O | 2-$CH_3$ | 2-$CH_3$ | H | H | —CHF—$CH_3$ | |
| 6.45 | S | H | H | H | H | —CO—$CH_3$ | HCl/mp. 173.0° C. |
| 6.46 | S | 2-$CH_3$ | 2-$CH_3$ | H | H | —$CH_2$—OH | |
| 6.47 | S | 2-$CH_3$ | 2-$CH_3$ | H | H | —CHO | |
| 6.48 | S | 2-$CH_3$ | 2-$CH_3$ | H | H | —CHOH—$CH_3$ | |
| 6.49 | S | 2-$CH_3$ | 2-$CH_3$ | H | H | —CO—$CH_3$ | |
| 6.50 | S | 2-$CH_3$ | 2-$CH_3$ | H | H | —$CH_2$—Cl | |
| 6.51 | S | 2-$CH_3$ | 2-$CH_3$ | H | H | —$CHF_2$ | |

TABLE 7

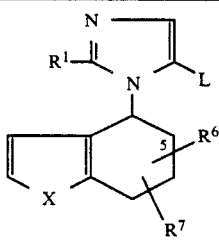

| Comp. No. | $R^1$ | $R^6$ | $R^7$ | X | L | Phys. data |
|---|---|---|---|---|---|---|
| 7.01 | H | H | H | S | —$CH_2OH$ | HCl/mp. 171.8° C. |
| 7.02 | H | H | H | S | —COH | $HNO_3$/mp. 127.4° C. |
| 7.03 | H | H | H | S | —CO—$C_2H_5$ | |
| 7.04 | H | H | H | S | —CO—$CH_3$ | |
| 7.05 | H | H | H | S | —CH(OH)—$C_2H_5$ | |
| 7.06 | H | 5-$CH_3$ | 5-$CH_3$ | S | —$CH_2$—OH | |

TABLE 7-continued

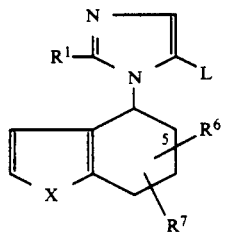

| Comp. No. | $R^1$ | $R^6$ | $R^7$ | X | L | Phys. data |
|---|---|---|---|---|---|---|
| 7.07 | H | 5-$CH_3$ | 5-$CH_3$ | S | —COH | |
| 7.08 | H | 5-$CH_3$ | 5-$CH_3$ | S | —CO—$C_2H_5$ | |
| 7.09 | H | H | H | O | —$CH_2OH$ | |
| 7.10 | H | H | H | O | —COH | |
| 7.11 | H | H | H | O | —CO—$C_2H_5$ | |
| 7.12 | H | H | H | O | —CH(OH)—$C_2H_5$ | |
| 7.13 | H | 5-$CH_3$ | 5-$CH_3$ | O | —$CH_2$—OH | |
| 7.14 | H | 5-$CH_3$ | 5-$CH_3$ | O | —COH | |
| 7.15 | H | 5-$CH_3$ | 5-$CH_3$ | O | —CO—$C_2H_5$ | |

TABLE 8

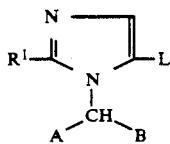

| Comp. No. | $R^1$ | A | B | L | Physical data |
|---|---|---|---|---|---|
| 8.01 | H | $C_3H_7$-n | 3-Cl—$C_6H_4$— | —$CH_2OH$ | |
| 8.02 | H | $C_3H_7$-n | 3-Cl—$C_6H_4$— | —COH | |
| 8.03 | H | $C_3H_7$-n | 3-Cl—$C_6H_4$— | —CO—$C_2H_5$ | |
| 8.04 | H | $C_3H_7$-n | 3-Cl—$C_6H_4$— | —CO—$CH_3$ | |
| 8.05 | H | $C_3H_7$-n | 3-Cl—$C_6H_4$— | —$CH_2$—O—$CH_3$ | |
| 8.06 | H | $C_3H_7$-n | 2-Cl—$C_6H_4$— | —$CH_2OH$ | |
| 8.07 | H | $C_3H_7$-n | 2-Cl—$C_6H_4$— | —COH | |
| 8.08 | H | $C_3H_7$-n | 2-Cl—$C_6H_4$— | —CO—$C_2H_5$ | |
| 8.09 | H | $C_3H_7$-n | 2-Cl—$C_6H_4$— | —$CH_2$—O—$CH_3$ | |
| 8.10 | H | $C_3H_7$-n | 2-Cl—$C_6H_4$— | —CO—$CH_3$ | |
| 8.11 | H | $C_3H_7$-n | $C_6H_5$— | —$CH_2OH$ | |
| 8.12 | H | $C_3H_7$-n | $C_6H_5$— | —COH | |
| 8.13 | H | $C_3H_7$-n | $C_6H_5$— | —CO—$C_2H_5$ | |
| 8.14 | H | $C_3H_7$-n | $C_6H_5$— | —CO—$CH_3$ | |
| 8.15 | H | benzyl | $C_6H_5$— | —$CH_2OH$ | |
| 8.16 | H | $C_3H_7$-n | 2-$CH_3$—$C_6H_4$— | —$CH_2OH$ | |
| 8.17 | H | $C_3H_7$-n | 2-$CH_3$—$C_6H_4$— | —COH | |
| 8.18 | H | $C_3H_7$-n | 2-$CH_3$—$C_6H_4$— | —CO—$C_2H_5$ | |
| 8.19 | H | 2-pyridinyl | $C_6H_5$— | —$CH_2OH$ | |
| 8.20 | H | 2-pyridinyl | $C_6H_5$— | —COH | |
| 8.21 | H | 2-pyridinyl | $C_6H_5$— | —CO—$C_2H_5$ | |
| 8.22 | H | 2-pyridinyl | $C_6H_5$— | —CO—$CH_3$ | 2 HCl.$H_2O$/ mp. 130° C. (dec.) |
| 8.23 | H | $C_3H_7$-i | 3-Cl—$C_6H_4$— | —$CH_2OH$ | |
| 8.24 | H | $C_3H_7$-i | 3-Cl—$C_6H_4$— | —COH | |
| 8.25 | H | $C_3H_7$-i | 3-Cl—$C_6H_4$— | —CO—$C_2H_5$ | |
| 8.26 | H | $C_3H_7$-i | 3-Cl—$C_6H_4$— | —CO—$CH_3$ | |
| 8.27 | H | $C_3H_7$-i | 3-Cl—$C_6H_4$— | —$CH_2$—O—$CH_3$ | |
| 8.28 | H | $C_6H_5$— | $C_6H_5$— | —COH | HCl/mp. 163.8° C. |
| 8.29 | H | $C_6H_5$— | $C_6H_5$— | —CO—$C_2H_5$ | |
| 8.30 | H | $C_6H_5$— | $C_6H_5$— | —CO—$CH_3$ | $HNO_3$/mp. 165.1° C. |
| 8.31 | H | $C_6H_5$— | $C_6H_5$— | —$CH_2$—O—$CH_3$ | |
| 8.32 | H | $C_6H_5$— | $C_6H_5$— | —$CH_2OH$ | mp. 148.4° C. |
| 8.33 | H | $CH_3$— | $C_6H_5$— | —$CH_2OH$ | mp. 102–103° C. |
| 8.34 | H | $CH_3$— | $C_6H_5$— | —$CH_2OH$ | .HCl/mp. 163–164° C. |
| 8.35 | H | $CH_3$— | $C_6H_5$— | —COH | mp. 65.5–66° C. |
| 8.36 | H | $CH_3$— | $C_6H_5$— | —$CH_2OCO$—$CH_3$ | .HCl/mp. 176–177° C. |
| 8.37 | H | $CH_3$— | $C_6H_5$— | —$CH_2$—O—$CH_3$ | .HCl/mp. 166.3° C. |
| 8.38 | H | $CH_3$— | $C_6H_5$— | —$CH_2$—NH—$CH_3$ | 2 HCl.$H_2O$/mp. 109° C. |
| 8.39 | H | $C_6H_5$— | $C_6H_5$— | —$CH_2OCO$—$CH_3$ | HCl/mp. 175.1° C. |
| 8.40 | H | $C_6H_5$— | $C_6H_5$— | —CH(OH)—$CH_3$ | mp. 141.1° C. |
| 8.41 | H | $C_6H_5$—$(CH_2)_2$— | $C_6H_5$— | —$CH_2OH$ | mp. 108.4° C. |
| 8.42 | H | $C_6H_5$— | $C_6H_5$— | —$CH_2Cl$ | |
| 8.43 | H | $C_6H_5$— | $C_6H_5$— | —$CH_2F$ | |

TABLE 8-continued

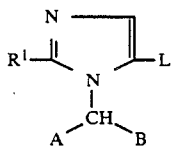

| Comp. No. | $R^1$ | A | B | L | Physical data |
|---|---|---|---|---|---|
| 8.44 | H | 2-pyridinyl | $C_6H_5-$ | $-CH_2Cl$ | |
| 8.45 | H | $C_6H_5$ | $C_6H_5-$ | $-CHF_2$ | |
| 8.46 | H | $C_6H_5$ | $C_6H_5-$ | $-CHCl-C_2H_5$ | |
| 8.47 | H | 2-pyridinyl | $C_6H_5-$ | $-CHF-CH_3$ | |
| 8.48 | H | $C_6H_5$ | $C_6H_5-$ | $-CHCl-CH_3$ | |
| 8.49 | H | $CH_3$ | $C_6H_5-$ | $-CH_2Cl$ | HCl/mp. 173.5–175° C. (dec.) |

TABLE 9

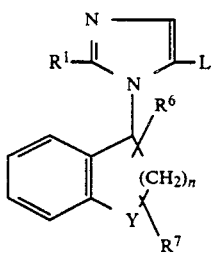

| Comp. No. | $R^1$ | $R^6$ | $R^7$ | Y | n | L | Physical data |
|---|---|---|---|---|---|---|---|
| 9.01 | H | H | H | O | 1 | $-CH_2OH$ | |
| 9.02 | H | H | H | O | 3 | $-CH_2OH$ | |
| 9.03 | H | H | H | O | 1 | $-CH_2O-CH_3$ | |
| 9.04 | H | H | H | O | 3 | $-CH_2O-CH_3$ | |
| 9.05 | H | H | H | O | 1 | $-COH$ | |
| 9.06 | H | H | H | O | 3 | $-COH$ | |
| 9.07 | H | H | H | O | 1 | $-CO-C_2H_5$ | |
| 9.08 | H | H | H | O | 3 | $-CO-C_2H_5$ | |
| 9.09 | H | H | H | O | 1 | $-CO-CH_3$ | |
| 9.10 | H | H | H | O | 3 | $-CO-CH_3$ | |
| 9.11 | SH | 2-$CH_3$ | 2-$CH_3$ | O | 1 | $-CH_2-OH$ | |
| 9.12 | H | 2-$CH_3$ | 2-$CH_3$ | O | 1 | $-CH_2-OH$ | |
| 9.13 | H | 2-$CH_2-CH_2$-2 | | O | 1 | $-CO-C_2H_5$ | |
| 9.14 | H | 2-$CH_3$ | 2-$CH_3$ | O | 1 | $-CH_2Cl$ | |
| 9.15 | H | 2-$CH_3$ | 2-$CH_3$ | O | 3 | $-CH_2Cl$ | |
| 9.16 | H | 2-$CH_3$ | 2-$CH_3$ | O | 1 | $-CHF_2$ | |
| 9.17 | H | 2-$CH_3$ | 2-$CH_3$ | O | 3 | $-CHF_2$ | |
| 9.18 | H | H | H | O | 1 | $-CHF_2$ | |
| 9.19 | H | H | H | O | 3 | $-CHF_2$ | |
| 9.20 | H | H | H | O | 1 | $-CHCl-C_2H_5$ | |
| 9.21 | H | H | H | O | 3 | $-CHF-C_2H_5$ | |
| 9.22 | H | 2-$CH_3$ | 2-$CH_3$ | O | 1 | $-COCH_3$ | $HNO_3$/mp. 165.6° C. |
| 9.23 | H | 2-$CH_3$ | 2-$CH_3$ | S | 1 | $-CH_2OH$ | |
| 9.24 | H | 2-$CH_3$ | 2-$CH_3$ | S | 1 | $-CHO$ | |
| 9.25 | H | 2-$CH_3$ | 2-$CH_3$ | S | 1 | $-COCH_3$ | |
| 9.26 | H | 2-$CH_3$ | 2-$CH_3$ | S | 1 | $-CH_2Cl$ | |
| 9.27 | H | 2-$CH_3$ | 2-$CH_3$ | S | 1 | $-CHF_2$ | |

TABLE 10

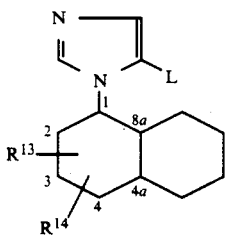

| Comp. No. | $R^{13}$ | $R^{14}$ | L | stereochemistry | Physical data |
|---|---|---|---|---|---|
| 10.01 | H | H | —CH$_2$—OH | (±)-[1α,4aα,8aβ] | mp. 130.1° C. |
| 10.02 | H | H | —CHO | (±)-[1α,4aα,8aβ] | .HCl/mp. 212.7° C. |
| 10.03 | H | H | —CHOH—CH$_3$ | (±)-[1α,4aα,8aβ] | mp. 120.9° C. |
| 10.04 | H | H | —CO—CH$_3$ | (±)-[1α,4aα,8aβ] | HNO$_3$/mp. 172.9° C. |
| 10.05 | H | H | —CHOH—CH$_2$CH$_3$ | (±)-[1α,4aα,8aβ] | |
| 10.06 | H | H | —CO—CH$_2$CH$_3$ | (±)-[1α,4aα,8aβ] | |
| 10.07 | 2-CH$_3$ | 2-CH$_3$ | —CH$_2$—OH | | |
| 10.08 | 2-CH$_3$ | 2-CH$_3$ | —CHO | | |
| 10.09 | 2-CH$_3$ | 2-CH$_3$ | —CHOH—CH$_3$ | | |
| 10.10 | 2-CH$_3$ | 2-CH$_3$ | —CO—CH$_3$ | | |
| 10.11 | 2-CH$_3$ | 2-CH$_3$ | —CHOH—CH$_2$—CH$_3$ | | |
| 10.12 | 2-CH$_3$ | 2-CH$_3$ | —CO—CH$_2$—CH$_3$ | | |
| 10.13 | H | H | —CH$_2$F | | |
| 10.14 | H | H | —CH$_2$Cl | | |
| 10.15 | H | H | —CHCl—CH$_3$ | | |
| 10.16 | H | H | —CHF—C$_2$H$_5$ | | |
| 10.17 | H | H | —CHF$_2$ | | |
| 10.18 | 2-CH$_3$ | 2-CH$_3$ | —CHF$_2$ | | |
| 10.19 | 2-CH$_3$ | 2-CH$_3$ | —CHCl—C$_2$H$_5$ | | |

TABLE 11

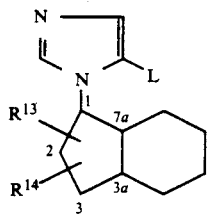

| Comp. No. | $R^{13}$ | $R^{14}$ | L | Physical data |
|---|---|---|---|---|
| 11.01 | H | H | CH$_2$OH | |
| 11.02 | H | H | COH | |
| 11.03 | H | H | CH(OH)CH$_3$ | |
| 11.04 | H | H | COCH$_3$ | |
| 11.05 | 2-CH$_3$ | 2-CH$_3$ | CH$_2$OH | |
| 11.06 | 2-CH$_3$ | 2-CH$_3$ | COH | |
| 11.07 | 2-CH$_3$ | 2-CH$_3$ | CH(OH)CH$_3$ | |
| 11.08 | 2-CH$_3$ | 2-CH$_3$ | COCH$_3$ | |
| 11.09 | 2-CH$_3$ | 2-CH$_3$ | CO(OH)C$_2$H$_5$ | |
| 11.10 | 2-CH$_3$ | 2-CH$_3$ | COC$_2$H$_5$ | |
| 11.11 | H | H | CH$_2$Cl | |
| 11.12 | H | H | CH$_2$Br | |
| 11.13 | H | H | CH$_2$F | |
| 11.14 | H | H | CHF$_2$ | |
| 11.15 | H | H | CF$_2$—CH$_3$ | |
| 11.16 | H | H | CHF—CH$_3$ | |
| 11.17 | H | H | CHCl—CH$_3$ | |

TABLE 12

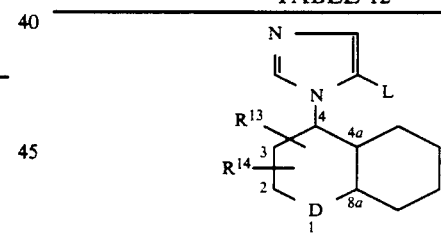

| Comp. No. | D | $R^{13}$ | $R^{14}$ | L | Physical data |
|---|---|---|---|---|---|
| 12.01 | O | H | H | CH$_2$OH | |
| 12.02 | O | H | H | COH | |
| 12.03 | O | H | H | CH(OH)CH$_3$ | |
| 12.04 | O | H | H | COCH$_3$ | |
| 12.05 | O | 2-CH$_3$ | 2-CH$_3$ | CH$_2$OH | |
| 12.06 | O | 2-CH$_3$ | 2-CH$_3$ | COH | |
| 12.07 | O | 2-CH$_3$ | 2-CH$_3$ | CH(OH)CH$_3$ | |
| 12.08 | O | 2-CH$_3$ | 2-CH$_3$ | COCH$_3$ | |
| 12.09 | S | H | H | CH$_2$OH | |
| 12.10 | S | H | H | COH | |
| 12.11 | S | H | H | CH(OH)CH$_3$ | |
| 12.12 | S | H | H | COCH$_3$ | |
| 12.13 | O | H | H | CH$_2$Cl | |
| 12.14 | S | H | H | CH$_2$Cl | |
| 12.15 | O | H | H | CHF$_2$ | |
| 12.16 | S | H | H | CHF$_2$ | |
| 12.17 | O | H | H | CHF—CH$_3$ | |
| 12.18 | S | H | H | CHCl—CH$_3$ | |
| 12.19 | O | H | H | CF$_2$—CH$_3$ | |
| 12.20 | S | H | H | CF$_2$—CH$_3$ | |

TABLE 13

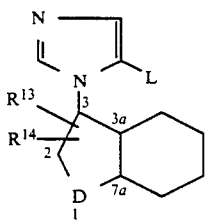

| Comp. No. | D | R13 | R14 | L | Physical data |
|---|---|---|---|---|---|
| 13.01 | O | H | H | $CH_2OH$ | |
| 13.02 | O | H | H | COH | |
| 13.03 | O | H | H | $CH(OH)CH_3$ | |
| 13.04 | O | H | H | $COCH_3$ | |
| 13.05 | O | 2-$CH_3$ | 2-$CH_3$ | $CH_2OH$ | |
| 13.06 | O | 2-$CH_3$ | 2-$CH_3$ | COH | |
| 13.07 | O | 2-$CH_3$ | 2-$CH_3$ | $CH(OH)CH_3$ | |
| 13.08 | O | 2-$CH_3$ | 2-$CH_3$ | $COCH_3$ | |
| 13.09 | S | 2-$CH_3$ | 2-$CH_3$ | $CH_2OH$ | |
| 13.10 | S | 2-$CH_3$ | 2-$CH_3$ | COH | |
| 13.11 | S | 2-$CH_3$ | 2-$CH_3$ | $CH(OH)CH_3$ | |
| 13.12 | S | 2-$CH_3$ | 2-$CH_3$ | $COCH_3$ | |

TABLE 14

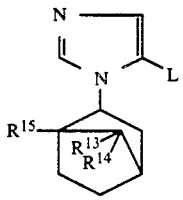

| Comp. No. | R13 | R14 | R15 | L | Physical data |
|---|---|---|---|---|---|
| 14.01 | $CH_3$ | $CH_3$ | $CH_3$ | —$CH_2$—OH | |
| 14.02 | $CH_3$ | $CH_3$ | $CH_3$ | —CHO | |
| 14.03 | $CH_3$ | $CH_3$ | $CH_3$ | —CHOH—$CH_3$ | |
| 14.04 | $CH_3$ | $CH_3$ | $CH_3$ | —CO—$CH_3$ | |
| 14.05 | $CH_3$ | $CH_3$ | $CH_3$ | —CHOH—$C_2H_5$ | |
| 14.06 | $CH_3$ | $CH_3$ | $CH_3$ | —CO—$C_2H_5$ | |
| 14.07 | $CH_3$ | $CH_3$ | $CH_3$ | —$CH_2$—OH | (1S,2RS,4S)/mp. 178.2° C. |
| 14.08 | $CH_3$ | $CH_3$ | $CH_3$ | —CHO | (1S,2RS,4S)/.HCl/mp. 205.9° C. |
| 14.09 | $CH_3$ | $CH_3$ | $CH_3$ | —CHOH—$CH_3$ | (1S,2RS,4S)/mp. 167.1° C. |
| 14.10 | $CH_3$ | $CH_3$ | $CH_3$ | —CO—$CH_3$ | (1S,2RS,4S)/$HNO_3$/mp. 196.1° C. |
| 14.11 | $CH_3$ | $CH_3$ | $CH_3$ | —CHOH—$C_2H_5$ | (1S,2RS,4S) |
| 14.12 | $CH_3$ | $CH_3$ | $CH_3$ | —CO—$C_2H_5$ | (1S,2RS,4S) |
| 14.13 | H | H | H | —$CH_2$—OH | |
| 14.14 | H | H | H | —CHO | |
| 14.15 | H | H | H | —CHOH—$CH_3$ | |
| 14.16 | H | H | H | —CO—$CH_3$ | |
| 14.17 | H | H | H | —CHOH—$C_2H_5$ | |
| 14.18 | H | H | H | —CO—$C_2H_5$ | |
| 14.19 | H | H | H | —$CF_2$—$C_2H_5$ | |
| 14.20 | $CH_3$ | $CH_3$ | $CH_3$ | —$CF_2$—$CH_3$ | |
| 14.21 | $CH_3$ | $CH_3$ | $CH_3$ | —$CH_2$F | |
| 14.22 | $CH_3$ | $CH_3$ | $CH_3$ | —$CH_2$Cl | |
| 14.23 | $CH_3$ | $CH_3$ | $CH_3$ | —$CHF_2$ | |
| 14.24 | $CH_3$ | $CH_3$ | $CH_3$ | —$CF_3$ | |
| 14.25 | H | H | H | —$CF_3$ | |

(B) COMPOSITION EXAMPLES

Example 22: Composition Examples for Solid Compounds of Formula (I) (Percentages are by Weight)

| (a) Wettable powders | (a) | (b) | (c) |
|---|---|---|---|
| compound of formula (I) | 20% | 50% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | 10% | — |
| sodium chloride | — | — | 59.5% |

The active ingredient was thoroughly mixed with the adjuvants and the mixture was thoroughly ground in a suitable mill, affording wettable powders which could be diluted with water to give suspensions of the desired concentration.

| (b) Emulsifiable concentrate | (a) | (b) |
|---|---|---|
| compound of formula (I) | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| dimethylbenzene mixture | 50% | 79% |

Emulsions of any required concentration could be obtained from this concentrate by dilution with water.

| (c) Dusts | (a) | (b) |
|---|---|---|
| compound of formula (I) | 0.1% | 1% |
| talcum | 99.9% | — |
| kaolin | — | 99% |

Usable dusts were obtained by mixing the active ingredient with the carriers, and grinding the mixture in a suitable mill.

| (d) Extruder granulate | (a) | (b) |
|---|---|---|
| compound of formula (I) | 10% | 1% |
| sodium lignosulfate | 2% | 2% |
| carboxymethylcellulose | 1% | 1% |
| kaolin | 87% | 96% |

The active ingredient was mixed and ground with the adjuvants, and the mixture was subsequently moistened with water. The mixture was extruded and dried in a stream of air.

| (e) Coated granulate | | |
|---|---|---|
| compound of formula (I) | | 3% |
| polyethylene glycol (mol. wt. 200) | | 2% |
| kaolin | | 95% |

The finely ground active ingredient was uniformly applied, in a mixer, to the kaolin moistened with polyethylene glycol. Non-dusty coated granulates were obtained in this manner.

| (f) Suspension concentrate | (a) | (b) |
|---|---|---|
| compound of formula (I) | 40% | 5% |
| ethylene glycol | 10% | 10% |
| nonylphenol polyethylene glycol ether (15 moles of ethylene oxide) | 6% | 1% |
| sodium lignosulfate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient was intimately mixed with the adjuvants, giving a suspension concentrate from which suspension of any desired concentration could be obtained by dilution with water.

| (g) Salt solution | |
|---|---|
| compound of formula (I) | 5% |
| isopropylamine | 1% |
| octylphenol polyethylene glycol ether (78 moles of ethylene oxide) | 3% |
| water | 91% |

Example 23: Composition Examples for Liquid Active Ingredients of Formula (I) (throughout, Percentages are by Weight)

| (a) Emulsifiable concentrates | (a) | (b) | (c) |
|---|---|---|---|
| compound of formula (I) | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| dimethylbenzene mixture | 70% | 25% | 20% |

Emulsions of any required concentration could be produced from such concentrate by dilution with water.

| (b) Solutions | (a) | (b) | (c) | (d) |
|---|---|---|---|---|
| compound of formula (I) | 80% | 10% | 5% | 95% |
| ethylene glycol monoethyl ether | 20% | — | — | — |
| polyethylene glycol (MG 400) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — |

These solutions were suitable for application in the form of microdrops.

| (c) Granulates | (a) | (b) |
|---|---|---|
| compound of formula (I) | 5% | 10% |
| kaolin | 94% | — |
| highly dispersed silicic acid | 1% | — |
| attapulgite | — | 90% |

The active ingredient was dissolved in dichloromethane, the solution was sprayed onto the carrier, and the solvent was subsequently evaporated off in vacuo.

| (d) Dusts | (a) | (b) |
|---|---|---|
| compound of formula (I) | 2% | 5% |
| highly dispersed silicic acid | 1% | 5% |
| talcum | 97% | — |
| kaolin | — | 90% |

Ready-for-use dusts were obtained by intimately mixing the carriers with the active ingredient.

C. Biological Examples

Example 24: Preemergence Herbicidal Action

In a greenhouse, immediately after sowing the test plants in seed dishes, the surface of the soil was treated with an aqueous dispersion of the test compounds, obtained from a 25% emulsifiable concentrate or from a 25% wettable powder with test compounds, which, on account of their insufficient solubility, could not be formulated to emulsifiable concentrates. The concentration corresponded to 4 kg of test compound per hectare. The seed dishes were kept in the greenhouse at 22°~25° C. and 50~70% relative humidity. The test was evaluated 3 weeks later in accordance with the following rating:

1 = plants had not germinated or were totally withered
2–3 = very strong action
4–6 = average action
7–8 = slight action
9 = no action.

Results: Preemergence test
Dosage: 4 kg active ingredient per hectare

| compound tested | plant tested | | | | | |
|---|---|---|---|---|---|---|
| | digitaria | poa | setaria | echinochloa | cynodon | maize |
| 1.10 (at 2 kg) | 1 | 1 | 1 | 1 | 1 | — |
| 2.07 | 1 | 1 | 1 | 1 | — | — |
| 2.08 | 1 | 1 | 1 | 1 | 1 | 9 |
| 2.12 | 1 | 1 | 1 | 1 | 1 | 9 |
| 2.13 | 1 | 1 | 1 | 1 | 3 | 9 |
| 2.46 | 1 | 1 | 1 | 1 | 1 | 9 |
| 2.48 | 1 | 1 | 1 | 1 | 1 | 9 |
| 2.51 | 1 | 1 | 1 | 1 | 1 | 9 |

-continued

| compound tested | plant tested | | | | | |
|---|---|---|---|---|---|---|
| | digi-taria | poa | setaria | echinochloa | cynodon | maize |
| 6.24 | 1 | 1 | 3 | 1 | 1 | 9 |
| 8.22 | 1 | 1 | 1 | 1 | 1 | — |
| 8.30 | 1 | 1 | 1 | 1 | 1 | 9 |
| 8.40 | 1 | 1 | 1 | 1 | 1 | 9 |
| 10.04 | 1 | 1 | 1 | 1 | 1 | 9 |

Example 25: Herbicidal Action against Paddy Rice associated Weeds

| Tested plant | Compound No. | | | | | | | | | | | | | | |
|---|---|---|---|---|---|---|---|---|---|---|---|---|---|---|---|
| | 1.10 in g a.i. per hectare | | | | | 2.08 in g a.i. per hectare | | | | | 8.40 in g a.i. per hectare | | | | |
| | 1000 | 500 | 250 | 125 | 60 | 1000 | 500 | 250 | 125 | 60 | 1000 | 500 | 250 | 125 | 60 |
| rice "Yamabiko" | 6 | 6 | 7 | 7 | 8 | 8 | 8 | 9 | 9 | 9 | 7 | 8 | 9 | 9 | 9 |
| echinochloa c.g. | 1 | 1 | 1 | 1 | 1 | 1 | 1 | 1 | 1 | 3 | 1 | 1 | 3 | 5 | 8 |
| scirpus | 1 | 1 | 1 | 1 | 1 | 1 | 1 | 2 | 4 | 5 | 1 | 1 | 2 | 5 | 5 |
| monochoria | 1 | 1 | 1 | 1 | — | 1 | 1 | 1 | 1 | 2 | 1 | 1 | 1 | 4 | 4 |

The seeds of the waterweeds Echinochloa crus galli and Monochoria vaginalis were sown together in plastic containers (60 cm² surface, 500 ml by volume). The containers were watered up to the soil surface and after three days the water level was raised slightly above the soil surface (3–5 mm). Three days after sowing an aqueous emulsion of the active compound was applied by spraying the containers at a rate of application of 4 kg of a.i. per hectare (dilution 550 l/ha). The containers were kept in a greenhouse for three weeks under conditions optimal for the waterweeds, i.e. at a temperature between 20° and 25° C. and under high humidity.

The evaluation of the tests was made in accordance with the rating given in example 24.

Results: dosage 4 kg active ingredient per hectare

| compound tested | plant tested | |
|---|---|---|
| | Echinochloa crus galli | Monchoria vaginalis |
| 1.10 | 1 | 1 |
| 2.04 | 1 | 1 |
| 2.08 | 1 | 1 |
| 2.10 | 1 | 1 |
| 2.12 | 1 | 1 |
| 2.13 | 1 | 1 |
| 2.14 | 1 | 1 |
| 2.37 | 1 | 1 |
| 2.45 | 1 | 1 |
| 2.46 | 1 | 1 |
| 2.47 | 2 | 1 |
| 2.48 | 1 | 1 |
| 2.54 | 2 | 1 |
| 6.24 | 1 | 1 |
| 7.01 | 5 | 1 |
| 7.02 | 3 | 4 |
| 8.22 | 1 | 1 |
| 8.28 | 5 | 1 |
| 8.30 | 1 | 1 |
| 8.32 | 1 | 1 |
| 8.39 | 1 | 1 |
| 8.40 | 1 | 1 |
| 14.07 | 2 | 2 |

Example 26: Herbicidal Action in Transplanted Rice Crops

25 Days old rice shoots of the variety "Yamabiko" were transplanted into large plastic containers. Into the same containers seeds of the weeds occuring in rice crops, namely echinochloa, scirpus and monochoria, were sown between the rice plants. The containers were watered to such an extent, that a water layer of 2.5 cm covered the surface. After 3 days under greenhouse conditions, the diluted aqueous dispersions of the active compounds were added to the water layer at a rate of application of 1000, 500, 250, 125 and 60 g a.i. per hectare. The containers were then kept covered with water at a temperature 25° C. and high humidity in a greenhouse for 4 weeks. The evaluation of the tests was made in accordance with the rating given in Example 24.

Results:

We claim:

1. A compound of the formula:

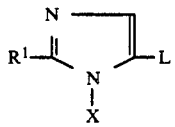

or a stereochemically isomeric form thereof, or a salt thereof, wherein:

$R^1$ represents hydrogen or mercapto;

L represents:

(ix) —C(=G)—R wherein G represents O or $NR^5$ wherein $R^5$ represents hydrogen, $C_{1-5}$alkyl, or hydroxy, and R represents hydrogen, $C_{1-7}$alkyl, or fluoro$C_{1-5}$alkyl; or (xi) —CH($R^3$)—$Z^1$—$R^4$ wherein $R^3$ represents hydrogen, $C_{1-5}$alkyl, or fluoro$C_{1-5}$alkyl, $R^4$ represents hydrogen or $C_{1-5}$alkyl, $Z^1$ represents O, S, or $NR^4$, and $R^4$ represents hydrogen or $C_{1-5}$alkyl, and X represents:

(o) a Group of the Formula:

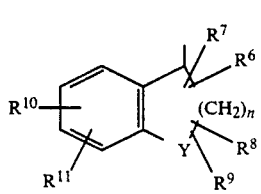

(a)

wherein Y represents —$CH_2$—O— or —$CH_2$—S—, n represents zero or one, $R^6$, $R^7$, $R^8$, and $R^9$ independently represent hydrogen or $C_{1-5}$alkyl, and $R^{10}$ and $R^{11}$ independently represent hydrogen or halo;

(p) a group of the Formula:

(b)

wherein A represents $C_{1-7}$alkyl, phenyl, or pyridinyl, said phenyl and pyridinyl being optionally substituted with $C_{1-5}$alkyl, methoxy, or halo, and B represents pyridinyl, phenyl, or phenyl substituted with $C_{1-5}$alkyl, methoxy, or halo; or (q) a group of the Formula:

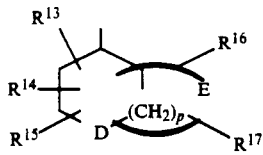

(c)

wherein D represents $CH_2$, O, or S, p represents 0 or 1, $R^{13}$, $R^{14}$, and $R^{15}$ represent hydrogen or $C_{1-5}$alkyl, E represents $C_{3-4}$alkanediyl, and $R^{16}$ and $R^{17}$ represent hydrogen or $C_{1-5}$alkyl.

2. A compound as described in claim 1 wherein $R^1$ represents hydrogen.

3. A compound as described in claim 1 wherein said compound is 1-(diphenylmethyl)-α-methyl-1H-imidazole-5-methanol.

4. A herbicidal composition comprising one or more inert carriers and a herbicidally effective amount of a compound of Formula (I) as described in claim 1.

5. A composition according to claim 4, wherein $R^1$ represents hydrogen.

6. A composition according to claim 4, wherein the active ingredient is 1-(diphenylmethyl)-alpha-methyl-1H-imidazole-5-methanol.

7. A method of controlling weeds by applying thereto or to the locus thereof of a herbicidally effective amount of a compound of Formula (I) as described in claim 1.

8. A method according to claim 7 wherein $R^1$ represents hydrogen.

9. A method according to claim 7 wherein the compound is 1-(diphenylmethyl)-alpha-methyl-1H-imidazole-5-methanol.

10. A method according to claim 7 for selectively controlling weeds in crops of useful plants.

11. A method according to claim 10 wherein the crop is rice, maize, or cereals.

12. A method according to claim 11 wherein the crop is rice and the rice is transplanted rice.

13. A method according to claim 12 wherein 0.01 to 5.0 kg of active ingredient per hectare are applied to areas where rice crops are grown.

14. A method according to claim 13 wherein 0.5 to 1 kg of the active ingredient is applied per hectare after transplanting the rice plantlets.

* * * * *